United States Patent
Karin et al.

(10) Patent No.: US 10,869,880 B2
(45) Date of Patent: Dec. 22, 2020

(54) METHODS FOR TREATING NLRP3 INFLAMMASOME-ASSOCIATED DISEASES, AND METHODS OF IDENTIFYING AGENTS USEFUL THEREFOR

(71) Applicant: The Regents of the University of California, Oakland, CA (US)

(72) Inventors: Michael Karin, La Jolla, CA (US); Zhenyu Zhong, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 16/451,674

(22) Filed: Jun. 25, 2019

(65) Prior Publication Data

US 2019/0388454 A1 Dec. 26, 2019

Related U.S. Application Data

(60) Provisional application No. 62/690,175, filed on Jun. 26, 2018.

(51) Int. Cl.
| | |
|---|---|
| *C07H 21/04* | (2006.01) |
| *A61K 31/713* | (2006.01) |
| *C12N 15/113* | (2010.01) |
| *A61K 9/127* | (2006.01) |
| *C12N 15/86* | (2006.01) |
| *A61K 9/14* | (2006.01) |

(52) U.S. Cl.
CPC ............ *A61K 31/713* (2013.01); *A61K 9/127* (2013.01); *A61K 9/14* (2013.01); *C12N 15/113* (2013.01); *C12N 15/86* (2013.01); *C12N 2310/11* (2013.01); *C12N 2310/122* (2013.01); *C12N 2310/141* (2013.01)

(58) Field of Classification Search
None
See application file for complete search history.

(56) References Cited

PUBLICATIONS

Tschopp, Jurg, and Kate Schroder. "NLRP3 inflammasome activation: The convergence of multiple signalling pathways on ROS production?." Nature reviews immunology 10.3 (2010): 210.*
He, Yuan, Hideki Hara, and Gabriel Núñez. "Mechanism and regulation of NLRP3 inflammasome activation." Trends in biochemical sciences 41.12 (2016): 1012-1021.*
Gross et al. "The inflammasome: an integrated view," Immunological Reviews, 2011, 243:136-151.
Grivennikov et al. "Immunity, Inflammation, and Cancer," Cell, Mar. 2010, 140:883-899.
Kotas et al. "Homeostasis, Inflammation, and Disease Susceptibility," Cell, Feb. 2015, 160:816-827.
Karin et al. "Reparative inflammation takes charge of tissue regeneration," Nature, Jan. 2016, 529:307-315.
Zhong et al. "Autophagy, Inflammation, and Immunity: A Troika Governing Cancer and Its Treatment," Cell, Jul. 2016, 166:288-298.
Lu et al. "Unified Polymerization Mechanism for the Assembly of ASC-Dependent Inflammasomes," Cell, Mar. 2014, 156:1193-1206.
Heneka et al. "Innate immune activation in neurodegenerative disease," Nature Reviews: Immunology, Jul. 2014, 14:463-477.
Lamkanfi et al. "Inflammasomes and Their Roles in Health and Disease," Annu. Rev. Cell Dev. Biol., 2012, 28:137-161.
Martinon et al. "The Inflammasomes: Guardians of the Body," Annu. Rev. Immunol., 2009, 27:229-265.
Schroder et al. "The Inflammasomes," Cell, Mar. 2010, 140:821-832.
Latz et al. "Activation and regulation of the inflammasomes," Nature Reviews: Immunology, Jun. 2013, 13:397-411.
Nakahira et al. "Autophagy proteins regulate innate immune response by inhibiting NALP3 inflammasome-mediated mitochondrial DNA release," Nat Immunol., Mar. 2011, 12(3):222-230.
Zhong et al. "NF-kB Restricts Inflammasome Activation via Elimination of Damaged Mitochondria," Cell, Feb. 2016, 164:896-910.
Zhou et al. "A role for mitochondria in NLRP3 inflammasome activation," Nature, Jan. 2011, 469:221-225.
Shimada et al. "Oxidized Mitochondrial DNA Activates the NLRP3 Inflammasome during Apoptosis," Immunity, Mar. 2012, 36:401-414.
Jiang et al. "Cytochrome C-Mediated Apoptosis," Annu. Rev. Biochem., 2004, 73:87-106.
Hamanaka et al. "Mitochondrial Reactive Oxygen Species Promote Epidermal Differentiation and Hair Follicle Development," Sci Signal, 2013, 6(261): ra8.
Hudson et al. "Mitochondrial DNA polymerase-gamma and human disease," Human Molecular Genetics, 2006, 15(2):R244-R252.
Kawai et al. "The role of pattern-recognition receptors in innate immunity: update on Toll-like receptors," Nature Immunology, May 2010, 11(5):373-384.
Ullah et al. "TRIF-dependent TLR signaling, its functions in host defense and inflammation, and its potential as a therapeutic target," Journal of Leukocyte Biology, Jul. 2016, 100:27-45.
Jehl et al. "IFNgamma Inhibits the Cytosolic Replication of Shigella flexneri via the Cytoplasmic RNA Sensor RIG-I," PLoS Pathogens, Aug. 2012, 8(8):e1002809.
Xu et al. "Human UMP-CMP Kinase 2, a Novel Nucleoside Monophosphate Kinase Localized in Mitochondria," The Journal of Biological Chemistry, Jan. 2008, 283(3):1563-1571.
Milon et al. "The Human nm23-H4 Gene Product Is a Mitochondrial Nucleoside Diphosphate Kinase," The Journal of Biological Chemistry, May 2000, 275(19):14264-14272.
Chen et al. "Identification of a putative human mitochondrial thymidine monophosphate kinase associated with monocytic/macrophage terminal differentiation," Genes to Cells, 2008, 13:679-689.
Subramanian et al. "The Adaptor MAVS Promotes NLRP3 Mitochondrial Localization and Inflammasome Activation," Cell, Apr. 2013, 153:348-361.
Elliot et al. "Initiation and perpetuation of NLRP3 inflammasome activation and assembly," Immunol Rev., May 2015, 265(1):35-52.
West et al. "TLR signalling augments macrophage bactericidal activity through mitochondrial ROS," Nature, Apr. 2011, 472:476-480.

\* cited by examiner

*Primary Examiner* — Kimberly Chong
(74) *Attorney, Agent, or Firm* — Foley & Lardner LLP

(57) ABSTRACT

Provided herein are methods of treating NLRP3 inflammasome-associated diseases and disorders. Also, disclosed are methods for screening for agents useful in such methods.

23 Claims, 18 Drawing Sheets
Specification includes a Sequence Listing.

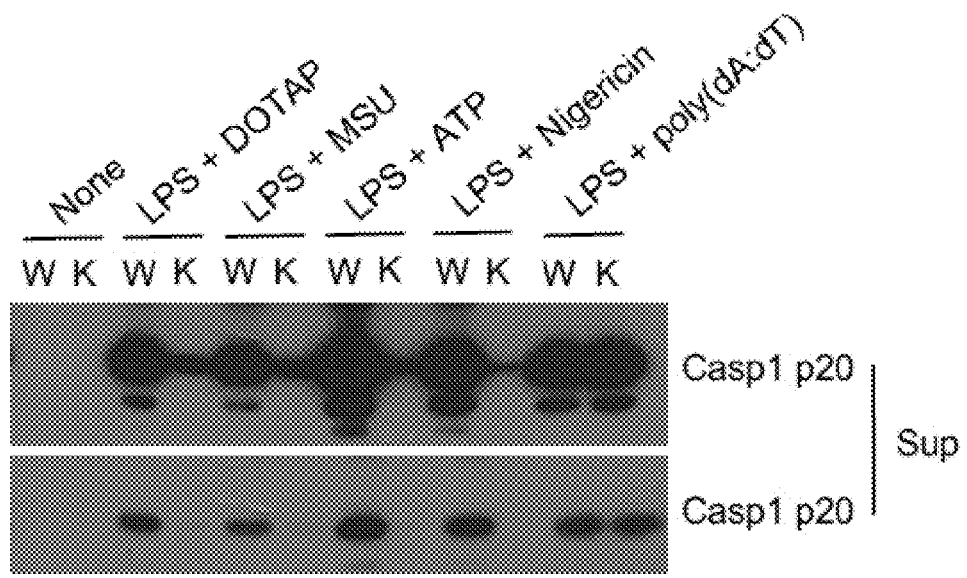
FIG. 2F
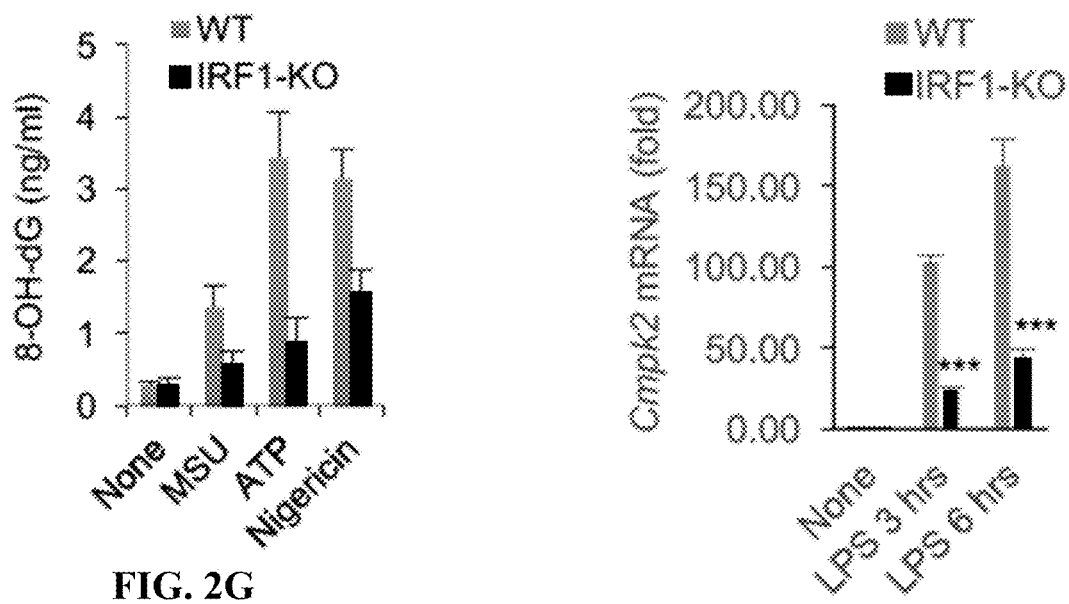
FIG. 2G
FIG. 3A

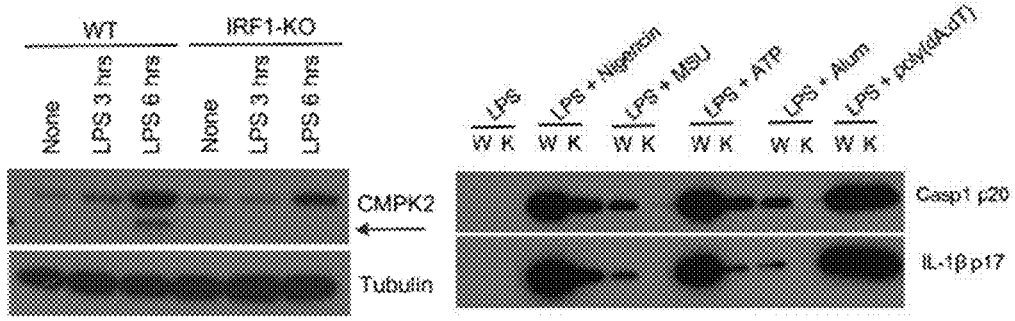
FIG. 3B  FIG. 3C
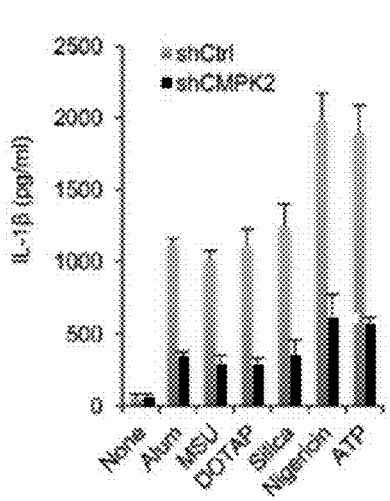 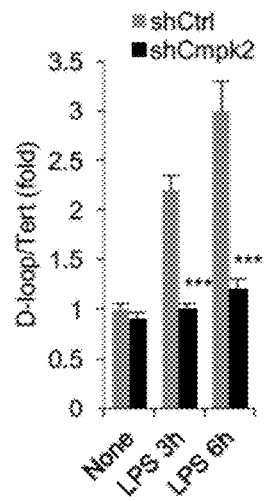 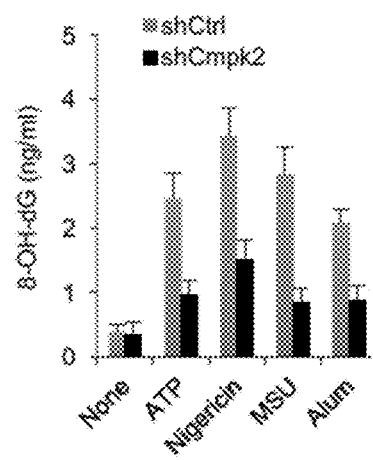
FIG. 3D  FIG. 3E  FIG. 3F

 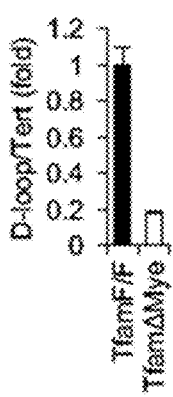 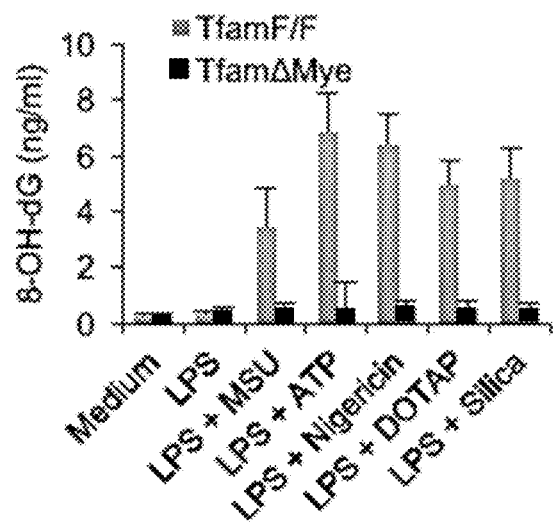
FIG. 6A  FIG. 6B  FIG. 6C
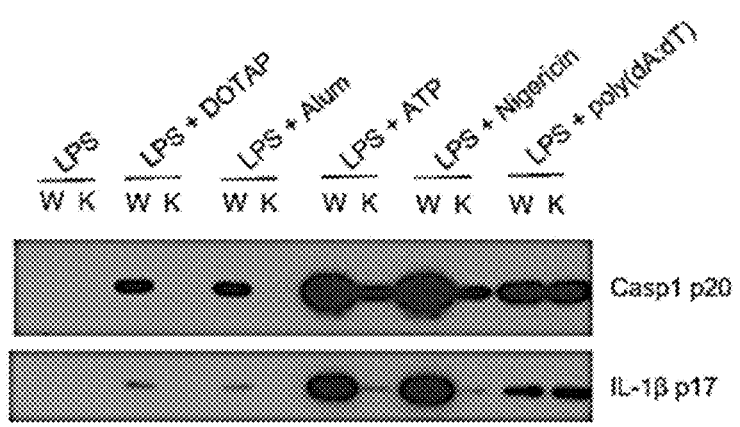
FIG. 6D

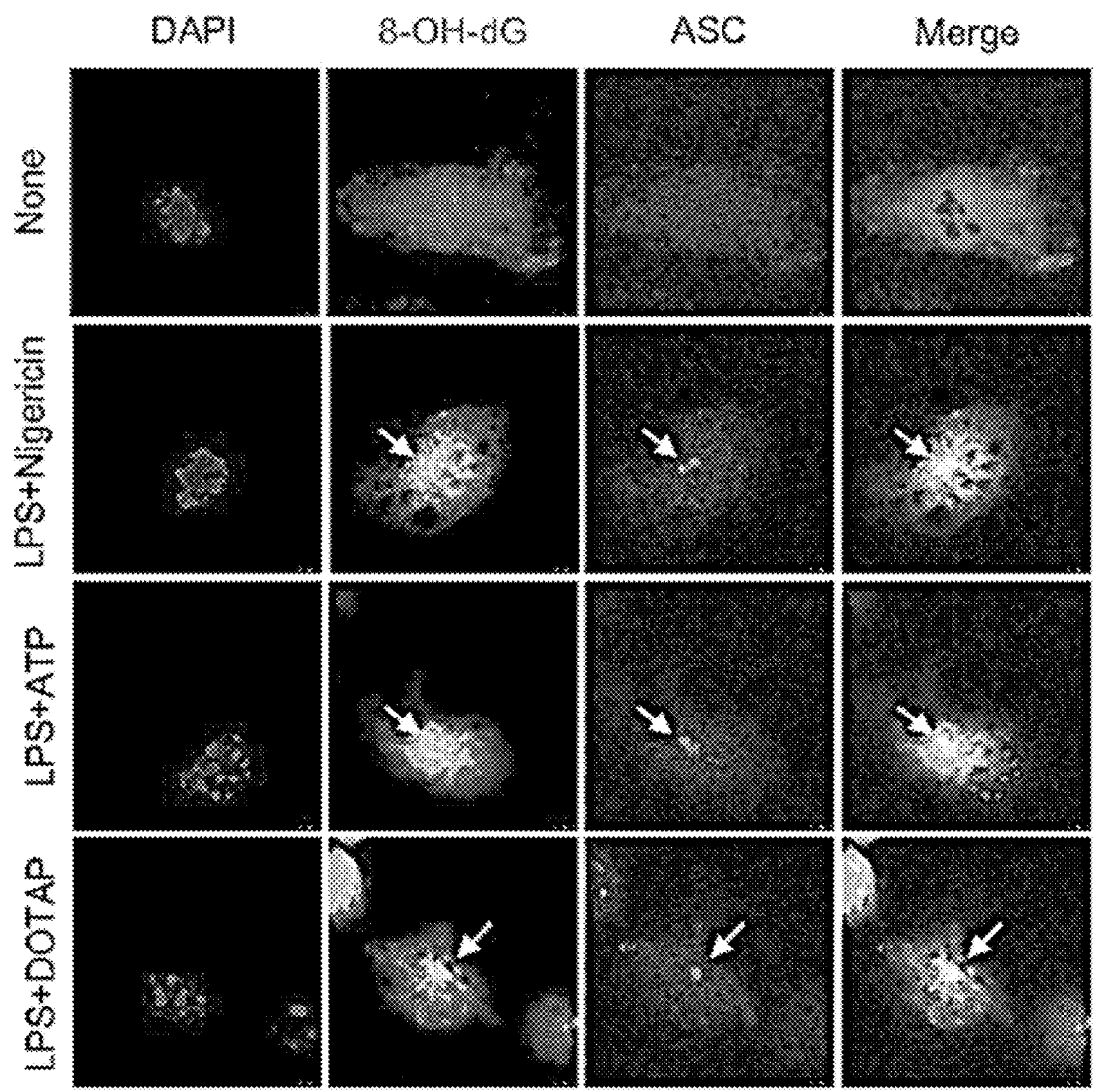
FIG. 6H
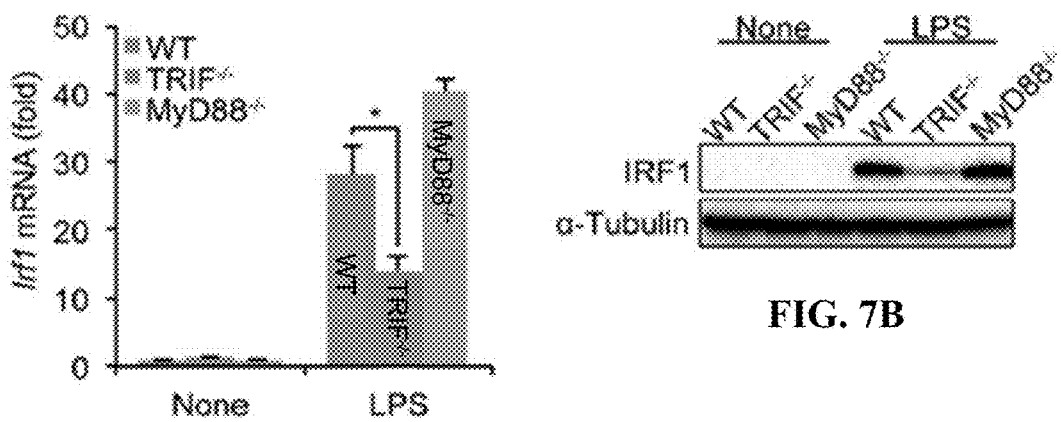
FIG. 7A
FIG. 7B

METHODS FOR TREATING NLRP3 INFLAMMASOME-ASSOCIATED DISEASES, AND METHODS OF IDENTIFYING AGENTS USEFUL THEREFOR

CROSS REFERENCE TO RELATED APPLICATION(S)

This application claims the benefit of priority under 35 U.S.C. § 119(e) of U.S. Ser. No. 62/690,175, filed Jun. 26, 2018, the entire content of which is incorporated herein by reference.

GRANT INFORMATION

This invention was made with government support under Grant Nos. AI043477 and ES010337 awarded by the National Institutes of Health. The United States government has certain rights in the invention.

SEQUENCE LISTING

The instant application contains a Sequence Listing which has been submitted electronically in ASCII format and is hereby incorporated by reference in its entirety. Said ASCII copy, created on Jun. 25, 2019, is named 20378-102261_SL.txt and is 8 kilobytes in size.

BACKGROUND OF THE INVENTION

Field of the Invention

The invention relates generally to inflammation and more specifically to methods and compositions for preventing NLRP3 inflammasome activation to treat inflammation and degenerative diseases.

Background Information

Chronic inflammation is involved in many different diseases including Alzheimer's disease, Parkinson's disease, Crohn's disease, myositis, inflammatory bowel disease, osteoarthritis, gout, rheumatoid arthritis, ankylosing spondylitis, uveitis, myositis, diverticulitis, dermatitis, colitis, autoimmune diseases, atherosclerosis, asthma, and cancer (Gross et al., 2011; Grivennikov, Greten and Karin, 2010). Inflammation is initiated upon sensing of pathogen (PAMP)- or damage (DAMP)-associated molecular patterns via pattern recognition receptors (PRR) (Gross et al., 2011; Kotas and Medzhitov, 2015). Amongst PRR, Nod-like receptor pyrin domain containing 3 (NLRP3) is unique in its ability to undergo activation in response to highly diverse extracellular stimuli, many of which, such as ATP and uric acid, are associated with tissue damage and can trigger sterile inflammation, which stimulates damage repair (Karin and Clevers, 2016; Zhong et al., 2016). Of note, NLRP3 is the sensor protein of an inflammasome complex that also contains the scaffold protein ASC and caspase-1, collectively referred to as the NLRP3 inflammasome (Gross et al., 2011).

Although the subject of intense efforts in academia and pharma alike, no effective strategies for inhibition of NLRP3 inflammasome activation and IL-1β production are clinically available. Moreover, the mechanism that triggers NLRP3 inflammasome activation remains poorly understood. A need therefore exists for treatments that prevent or ameliorate NLRP3 inflammasome-dependent diseases and attenuate their progression.

SUMMARY OF THE INVENTION

The present invention is based on the observation that activation of the NLRP3 inflammasome depends on a specific signal generated by oxidized mitochondrial (mt) DNA and interference with the generation of this signal is capable of inhibiting NLRP3 inflammasome-driven inflammation. Accordingly, in one aspect, the invention provides a method of treating NLRP3 inflammasome-associated inflammatory and/or degenerative diseases or cancers in a subject. The method includes administering to a subject in need thereof an effective amount of an inhibitor of NLRP3 inflammasome activation. In various embodiments, the inhibitor of NLRP3 inflammasome activation inhibits interferon regulatory factor 1 (IRF1) activity or expression and/or cytidine monophosphate kinase 2 (CMPK2) activity or expression. In various embodiments, the subject is a mammal, such as a human. In various embodiments, the inhibitor of CMPK2 activity or expression is a small molecule, peptide, antisense oligonucleotide, RNA hairpin, guide DNA, antibody or an antibody fragment. In various embodiments, the inhibitor of CMPK2 activity or expression is an inhibitory nucleic acid that inhibits the expression of CMPK2. In various embodiments, the inhibitory nucleic acid is selected from the group consisting of siRNA, shRNA, gRNA, oligonucleotides, antisense RNA or ribozymes that inhibit CMPK2 synthesis. In various embodiments, the inhibitory nucleic acid is administered via a viral vector, a liposome or a nanoparticle. In various embodiments, the NLRP3 inflammasome-associated inflammatory and/or degenerative disease is selected from the group consisting of cancer (especially lung cancer), lupus, gout, rheumatoid arthritis, osteoarthritis, ankylosing spondylitis, uveitis, Alzheimer's disease, Parkinson's disease, cryopyrin-associated periodic syndromes, nonalcoholic steatohepatitis (NASH), type 2 diabetes, atherosclerosis, macular degeneration, and geographical retinopathy.

In another aspect, the invention provides a method of inhibiting NLRP3 inflammasome activation in a subject. The method includes administering to the subject an effective amount of an inhibitor of CMPK2 activity or expression. In various embodiments, the inhibitor of CMPK2 activity or expression is a small molecule, peptide, antisense oligonucleotide, antibody or an antibody fragment. In various embodiments, the inhibitor of CMPK2 activity or expression is an inhibitory nucleic acid that inhibits the expression of CMPK2 or inhibits CMPK2 synthesis. In various embodiments, the inhibitor nucleic acid is selected from the group consisting of siRNA, shRNA, gRNA, oligonucleotides, antisense RNA or ribozymes that inhibit CMPK2 synthesis. In various embodiments, the inhibitory nucleic acid is administered via a viral vector, liposome or a nanoparticle.

In another aspect, the invention provides a method of identifying an agent that inhibits NLRP3 inflammasome activation through the targeting of either IRF1 or CMPK2. The method includes contacting a sample of cells with at least one test agent, wherein a decrease in CMPK2 activity or expression in the presence of the test agent as compared to CMPK2 activity or expression in the absence of the test agent identifies the agent as useful for inhibiting NLRP3 inflammasome activation by virtue of its ability to reduce CMPK2 activity or expression. In various embodiments, the test agent is a small molecule, peptide, antisense oligonucleotide, antibody or an antibody fragment. In various embodiments, the method may be performed in a high throughput format, such as contacting samples of cells of a plurality of samples with at least one test agent. In various embodiments, the plurality of samples may be obtained from a single subject or from different subjects. In other embodiments, the CMPK2 targeting agent is selected from a library of known nucleotide kinase inhibitors.

BRIEF DESCRIPTION OF THE DRAWINGS

FIG. 1A shows that shCtrl or shNlrp3 transduced Tfam$^{\Delta mye}$ (i.e., TFAM-deficient) bone marrow derived macrophages (BMDM) were incubated with LPS, synthetic Ox-mtDNA or LPS+ synthetic Ox-mtDNA. The release of IL-1β to culture supernatants was measured 4 hrs later. Data are averages±s.d. (n=3). FIG. 1B shows that relative amounts of total mtDNA were quantified by qPCR using primers specific for mtDNA (cytochrome c oxidase I, and D-loop) and nuclear (n)DNA (18S and Tert) in WT BMDM before and after LPS (200 ng/ml) treatment. Data are averages±s.d. (n=3). FIG. 1C shows representative immunofluorescent (IF) staining of EdU-labeled newly synthesized mtDNA in WT BMDM before and after LPS stimulation. Scale bars 5 μm. Images representative of 3 independent experiments. FIG. 1D shows relative levels of total mtDNA in immortalized BMDM (iBMDM) transduced with shCtrl or shPolg RNAs before and after LPS treatment. Data are averages±s.d. (n=3). FIG. 1E shows relative amounts of total mtDNA in WT, Myd88$^{-/-}$ and Trif$^{-/-}$ before and after LPS stimulation were qPCR determined. Data are averages±s.d. (n=3). FIG. 1F shows relative amounts of total mtDNA in WT and Ifnar1$^{-/-}$ BMDM before and after LPS stimulation were qPCR determined. Data are averages±s.d. (n=3).

FIGS. 2A-2G are pictorial and graphical diagrams showing that IRF1 controls mtDNA synthesis, Ox-mtDNA generation and NLRP3 inflammasome activation. FIG. 2A shows relative amounts of total mtDNA that were quantified by qPCR using primers specific for mtDNA (D-loop) and nDNA (Tert) in WT and Irf1$^{-/-}$ BMDM that were stimulated with LPS as indicated. The amounts of mtDNA in these cells were quantified by qPCR using the medicated primers. Data are averages±s.d. (n=3). FIG. 2B shows relative amounts of total mtDNA that were quantified by qPCR using primers specific for mtDNA (cytochrome c oxidase I) and nDNA (18S) in WT and Irf1$^{-/-}$ BMDM were stimulated with LPS as indicated. The amounts of mtDNA in these cells were quantified by qPCR using the indicated primers. Data are averages±s.d. (n=3). FIG. 2C shows representative images showing EdU incorporation into mtDNA in WT and Irf1$^{-/-}$ BMDM incubated without or with LPS. Scale bars 5 μm. FIG. 2D shows quantification of the fraction of cells showing mtDNA replication as determined in FIG. 2C. Averages±s.d. (n=257~313). FIG. 2E shows immunoblot (IB) analysis of cleaved caspase-1 (Casp1 p20) released into culture supernatants of WT and Irf1$^{-/-}$ BMDM that were treated with LPS plus indicated inflammasome activators. W=WT; K=Irf1$^{-/-}$. FIG. 2F shows IL-1β in culture supernatants of LPS-primed WT and Irf1$^{-/-}$ BMDM that were treated with LPS and the indicated NLRP3 activators. Data are averages±s.d. (n=3). FIG. 2G shows amounts of 8-OH-dG in mtDNA isolated from LPS-primed WT and Irf1$^{-/-}$ BMDM that were treated with LPS and the indicated NLRP3 activators. Data are averages±s.d. (n=3).

FIGS. 3A-3F are pictorial and graphical diagrams showing that CMPK2 controls mtDNA synthesis, Ox-mtDNA generation and NLRP3 inflammasome activation. FIG. 3A shows relative amounts of Cmpk2 mRNA in WT and Irf1$^{-/-}$ BMDM before and after LPS stimulation. Data are averages±s.d. (n=3). FIG. 3B shows immunoblot (IB) analysis of CMPK2 in WT and Irf1$^{-/-}$ BMDM before and after LPS stimulation. The arrow points to the CMPK2 band. FIG. 3C shows IB analysis of Casp1 p20 and mature IL-1β (p17) in supernatants of shCtrl (W) and shCmpk2 (K) BMDM that were stimulated with LPS plus the indicated inflammasome agonists. FIG. 3D shows IL-1β secretion by LPS-primed shCtrl and shCmpk2 BMDM that were treated with the indicated NLRP3 agonists. Data are averages±s.d. (n=3). FIG. 3E shows relative amounts of total mtDNA in shCtrl and shCmpk2 BMDM before and after LPS stimulation. Data are averages±s.d. (n=3). FIG. 3F shows amounts of 8-OH-dG (oxidized deoxy-guanosine) in mtDNA isolated from LPS-primed WT and Irf1$^{-/-}$ BMDM that were treated with indicated NLRP3 activators. Data are averages±s.d. (n=3).

FIG. 4A shows relative amounts of total mtDNA in LPS-treated WT and Irf1$^{-/-}$ BMDM that were transduced with WT Cmpk2 or empty lentiviruses. Data are averages±s.d. (n=3). FIG. 4B shows IL-1β secretion by CMPK2 lentivirus-transduced WT and Irf1$^{-/-}$ BMDM that were stimulated with LPS+ATP or LPS+MSU. Data are averages±s.d. (n=3). FIG. 4C shows relative amounts of total mtDNA in LPS-treated WT and Irf1$^{-/-}$ BMDM that were transduced with either WT Cmpk2 or Cmpk2(D330A) lentiviruses. Data are averages±s.d. (n=3). FIG. 4D shows IL-1β secretion by WT Cmpk2 or Cmpk2 (D330A)-reconstituted WT and Irf1$^{-/-}$ BMDM that were stimulated as indicated. Data are averages±s.d. (n=3).

FIGS. 6A-6H are pictorial and graphical diagrams showing that TFAM is required for maintenance of mtDNA, generation of Ox-mtDNA, and activation of the NLRP3 inflammasome. FIG. 6A shows that relative amounts of total mtDNA in Tfam$^{F/F}$ and Tfam$^{\Delta mye}$ BMDM were quantified by qPCR using primers specific for mtDNA (cytochrome c oxidase I) and nDNA (18S). Data are averages±s.d. (n=3). FIG. 6B shows that relative amounts of total mtDNA in Tfam$^{F/F}$ and Tfam$^{\Delta mye}$ BMDM were quantified by qPCR using primers specific for mtDNA (D-loop) and nDNA (Tert). Data are averages±s.d. (n=3). FIG. 6C shows amounts of 8-OH-dG in mtDNA isolated from Tfam$^{F/F}$ and Tfam$^{\Delta Mye}$ BMDM that were stimulated with LPS plus various NLRP3 activators. Data are averages±s.d. (n=3). FIG. 6D shows IB analysis of Casp1 p20 and mature IL-1β (p17) in culture supernatants of Tfam$^{F/F}$ (W) and Tfam$^{\Delta Mye}$ (K) BMDM that were stimulated with LPS plus various inflammasome activators. Results are typical of three separate experiments. FIG. 6E shows IB analysis of pro-IL-1β, NLRP3, ASC, and pro-Casp1 in lysates of Tfam$^{F/F}$ and Tfam$^{\Delta Mye}$ BMDM before and after LPS priming. Results are typical of three separate experiments. FIG. 6F shows amounts of IL-1β in culture supernatants of LPS-primed Tfam$^{F/F}$ and Tfam$^{\Delta Mye}$ BMDM that were stimulated with various NLRP3 activators. Data are averages±s.d. (n=3). FIG. 6G shows amounts of TNF in culture supernatants of LPS-primed Tfam$^{F/F}$ and Tfam$^{\Delta Mye}$ BMDM that were stimulated with various NLRP3 agonists. Data are averages±s.d. (n=3). FIG. 6H shows representative IF images of WT BMDM that were co-stained with 8-OH-dG, ASC and DAPI before and after stimulation with LPS plus the indicated inflammasome agonists. Scale bars, 5 µm.

FIGS. 7A-7G are pictorial and graphical diagrams showing that IRF1 does not affect inflammasome subunit expression nor NLRP3 agonist-induced mitochondrial damage. FIG. 7A shows relative amounts of Irf1 mRNA in WT, Trif$^{-/-}$ and MyD88$^{-/-}$ BMDM before and after LPS stimulation. Data are averages±s.d. (n=3). FIG. 7B shows IB analysis of IRF1 in lysates of WT, Trif$^{-/-}$ and MyD88$^{-/-}$ BMDM before and after LPS priming. Results are typical of 3 separate experiments. FIG. 7C shows relative amounts of Irf1 mRNA in WT and Ifnar1$^{-/-}$ BMDM before and after LPS priming. Data are averages s.d. (n=3). FIG. 7D shows IB analysis of pro-IL-1β, NLRP3, ASC, and pro-Casp1 in lysates of WT and Irf1$^{-/-}$ BMDM before and after LPS priming. Results are typical of 3 separate experiments. FIG. 7E shows TNF secretion by LPS-primed WT and Irf1$^{-/-}$ BMDM that were stimulated with various NLRP3 activators. Data are averages±s.d. (n=3). FIG. 7F shows NLRP3 activator-induced changes in mitochondrial membrane potential (Ψm) in LPS-primed WT and Irf1$^{-/-}$ BMDM were measured by TMRM fluorescence. Data are averages±s.d. (n=3). FIG. 7G shows relative amounts of mtROS were measured by MitoSOX fluorescence in LPS-primed WT and Irf1$^{-/-}$ BMDM after stimulation with various NLRP3 activators. Data are averages±s.d. (n=3).

FIG. 8A shows relative amounts of Cmpk2 mRNA in WT and Trif$^{-/-}$ BMDM before and after LPS stimulation. Data are averages±s.d. (n=3). FIG. 8B shows relative amounts of Cmpk2 mRNA in WT and Ifnar1$^{-/-}$ BMDM before and after LPS stimulation. Data are averages±s.d. (n=3). IB analysis of CMPK2 in lysates of WT and Ifnar1$^{-/-}$ BMDM before and after LPS stimulation. Results are typical of three separate experiments. FIG. 8D shows the Cmpk2 promoter contains IRF1 binding sites (site 1, SEQ ID NO: 3; site 2, SEQ ID NO: 4; site 3, SEQ ID NO: 5).

FIG. 9 shows relative mRNA amounts of dGK, Tk2, Ak2, Nme4, and Polg in WT BMDM before and after LPS stimulation. Data are averages±s.d. (n=3).

FIG. 10A shows IB analysis of CMPK2, pro-IL-1β, NLRP3, ASC, and pro-Casp1 in lysates of WT (shCtrl) and CMPK2-deficient (shCmpk2) BMDM before and after LPS priming. Results are typical of 3 separate experiments. FIG. 10B shows NLRP3 activator-induced changes in Ψm in LPS-primed shCtrl and shCmpk2 BMDM were measured by TMRM fluorescence. Data are averages±s.d. (n=3). FIG. 10C shows relative amounts of mtROS measured by MitoSOX fluorescence in LPS-primed shCtrl and shCmpk2 BMDM after stimulation with various NLRP3 activators. Data are averages±s.d. (n=3).

FIG. 11A shows relative amounts of total mtDNA in shCtrl and shNme4 BMDM before and after LPS priming. Data are averages±s.d. (n=3). FIG. 11B shows amounts of 8-OH-dG in mtDNA isolated from shCtrl and shNme4 BMDM that were stimulated or not with LPS plus various NLRP3 activators. Data are averages±s.d. (n=3). FIG. 11C shows amounts of IL-1β in supernatants of LPS-primed shCtrl and shNme4 BMDM that were stimulated with various inflammasome activators. Data are averages±s.d. (n=3). FIG. 11D shows amounts of TNF in supernatants of LPS-primed shCtrl and shNme4 BMDM that were stimulated with various inflammasome activators. Data are averages±s.d. (n=3).

FIG. 12A shows NLRP3 activator-induced changes in Ψm in LPS-primed CMPK2-transduced WT and Irf1$^{-/-}$ BMDM were measured by TMRM fluorescence. Data are averages±s.d. (n=3). FIG. 12B shows relative amounts of mtROS measured by MitoSOX fluorescence in LPS-primed CMPK2-transduced WT and Irf1$^{-/-}$ BMDM before and after stimulation with ATP or nigericin. Data are averages±s.d. (n=3). IB analysis of Casp1 p20 and mature IL-1 (3 (p17) in supernatants of LPS-primed CMPK2-transduced WT and Irf1$^{-/-}$ BMDM before and after stimulation with various NLRP3 activators.

FIG. 13A shows 12-week old WT or Irf1$^{-/-}$ mice were i.p. injected with LPS and their sera collected 3 hrs later and analyzed by ELISA for IL-1β. Results are averages±s.d. (n=8). FIG. 13B shows 12-week old WT or Irf1$^{-/-}$ mice were i.p. injected with LPS and their sera collected 3 hrs later and analyzed by ELISA for TNF. Results are averages±s.d. (n=8). FIG. 13C shows survival of WT or Irf1$^{-/-}$ mice that were i.p. injected with LPS (50 mg/kg), n=10-11. FIG. 13D shows relative amounts of total mtDNA in peritoneal infiltrates of WT or Irf1$^{-/-}$ mice and before and after LPS (50 mg/kg) injection. Data are averages±s.d. (n=3). FIG. 13E shows peritoneal IL-1β in WT or Irf1$^{-/-}$ mice 4 hrs after i.p. injection of alum (300 µg) or PBS. n=3-6. FIG. 13F shows proteinuria was measured in urine of WT or Irf1$^{-/-}$ female mice before and 12 hrs after i.p. injection with 300 mg/Kg folic acid. Data are shown as mean±s.e.m. of 5-10 mice. **, p<0.01. Results are representative of kidney extracts from three mice per group. Alum-induced peritoneal infiltration of neutrophils (CD11b$^+$ Ly6G$^+$F4/80$^-$). Biochemical analysis of protein, creatine, BUN and electrolytes levels in sera of the mice. Data are mean±s.e.m. of 5-10 mice. Representative H&E staining of kidney sections from treated mice. IB analysis of casp1 p20, mature IL-1β, IRF1, CMPK2 and tubulin in the whole kidney extracts from mice treated as in h. Results are representative of kidney extracts from three mice per group.

DETAILED DESCRIPTION OF THE INVENTION

Figure 1A:
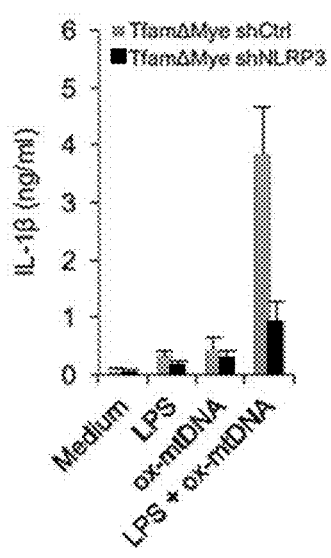
FIGS. 1A-1F are graphical and pictorial diagrams showing that mitochondrial (mt) DNA, whose replication is stimulated by occupancy of Toll-like receptors (TLR), is needed for activation of the NLRP3 inflammasome.

The present invention is based on the observation that persistent activation of the NLRP3 inflammasome results in uncontrolled inflammation that contributes to the pathogenesis of many chronic and acute inflammatory and degenerative diseases. Thus, without being bound by theory, NLRP3 appears to be the key sensor of tissue damage and mediator of sterile inflammation, playing a central role in the pathogenesis of acute and chronic inflammatory diseases.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

As used herein, a "non-human mammal" may be any animal as long as it is other than human, and includes a transgenic animal and animals for which a production method of ES cells and/or iPS cells has been established. For example, rodents such as mouse, rat, hamster, guinea pig, rabbit, swine, bovine, goat, horse, sheep, dog, cat, or monkey are envisioned as non-human mammals.

The terms "administration" or "administering" are defined to include an act of providing a compound or pharmaceutical composition of the invention to a subject in need of treatment. The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion. The phrases "systemic administration," "administered systemically," "peripheral administration" and "administered peripherally" as used herein mean the administration of a compound, drug or other material other than directly into the central nervous system, such that it enters the subject's system and, thus, is subject to metabolism and other like processes, for example, subcutaneous administration or administration via intranasal delivery.

As used herein, an "effective amount" is an amount of a substance or molecule sufficient to effect beneficial or desired clinical results including alleviation or reduction in any one or more of the symptoms associated with NLRP3 inflammasome-driven inflammation such as, but not limited to, cancer, lupus, gout, rheumatoid arthritis, osteoarthritis, ankylosing spondylitis, uveitis, Alzheimer's disease, Parkinson's disease, cryopyrin-associated periodic syndromes, nonalcoholic steatohepatitis (NASH), type 2 diabetes, atherosclerosis, macular degeneration, and many more inflammatory and degenerative diseases. For purposes of this invention, an effective amount of a compound or molecule of the invention is an amount sufficient to reduce the signs and symptoms associated with such disorders. In some embodiments, the "effective amount" may be administered before, during, and/or after any treatment regimens for the above-mentioned diseases.

As used herein, "treatment" is an approach for obtaining beneficial or desired clinical results. For purposes of this invention, beneficial or desired clinical results include, but are not limited to, treatment of NLRP3 inflammasome-associated diseases or disorders.

As used herein, the term "genetic modification" is used to refer to any manipulation of an organism's genetic material in a way that does not occur under natural conditions. Methods of performing such manipulations are known to those of ordinary skill in the art and include, but are not limited to, techniques that make use of vectors for transforming cells with a nucleic acid sequence of interest. Included in the definition are various forms of gene editing in which DNA is inserted, deleted or replaced in the genome of a living organism using engineered nucleases, or "molecular scissors." These nucleases create site-specific double-strand breaks (DSBs) at desired locations in the genome. The induced double-strand breaks are repaired through nonhomologous end-joining (NHEJ) or homologous recombination (HR), resulting in targeted mutations (i.e., edits). There are several families of engineered nucleases used in gene editing, for example, but not limited to, meganucleases, zinc finger nucleases (ZFNs), transcription activator-like effector-based nucleases (TALEN), and the CRISPR-Cas system.

As used herein, the term "test agent" or "candidate agent" refers to an agent that is to be screened in one or more of the assays described herein. The agent can be virtually any chemical compound. It can exist as a single isolated compound or can be a member of a chemical (e.g., combinatorial) library. In one embodiment, the test agent is a small organic molecule. The term small organic molecule refers to any molecules of a size comparable to those organic molecules generally used in pharmaceuticals. The term excludes biological macromolecules (e.g., proteins, nucleic acids, etc.). In certain embodiments, small organic molecules range in size up to about 5000 Da, up to 2000 Da, or up to about 1000 Da.

As used herein, the terms "sample" and "biological sample" refer to any sample suitable for the methods provided by the present invention. In one embodiment, the biological sample of the present invention is a tissue sample, e.g., a biopsy specimen such as samples from needle biopsy (i.e., biopsy sample). In other embodiments, the biological sample of the present invention is a sample of bodily fluid, e.g., serum, plasma, sputum, lung aspirate, urine, and ejaculate.

The term "antibody" is meant to include intact molecules of polyclonal or monoclonal antibodies, chimeric, single chain, and humanized antibodies, as well as fragments thereof, such as Fab and F(ab')2, Fv and SCA fragments which are capable of binding an epitopic determinant. Monoclonal antibodies are made from antigen containing fragments of the protein by methods well known to those skilled in the art (Kohler, et al., Nature, 256:495, 1975). An Fab fragment consists of a monovalent antigen binding fragment of an antibody molecule, and can be produced by digestion of a whole antibody molecule with the enzyme papain, to yield a fragment consisting of an intact light chain and a portion of a heavy chain. An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner. An (Fab')2 fragment of an antibody can be obtained by treating a whole antibody molecule with the enzyme pepsin, without subsequent reduction. A (Fab')2 fragment is a dimer of two Fab' fragments, held together by two disulfide bonds. An Fv fragment is defined as a genetically engineered fragment containing the variable region of a light chain and the variable region of a heavy chain expressed as two chains. A single chain antibody ("SCA") is a genetically engineered single chain molecule containing the variable region of a light chain and the variable region of a heavy chain, linked by a suitable, flexible polypeptide linker.

Reference herein to "normal cells" or "corresponding normal cells" means cells that are from the same organ and of the same type as any of the above-mentioned disease cell type. In one aspect, the corresponding normal cells comprise a sample of cells obtained from a healthy individual. Such corresponding normal cells can, but need not be, from an individual that is age-matched and/or of the same sex as the individual providing the above-mentioned disease cells being examined. In another aspect, the corresponding normal cells comprise a sample of cells obtained from an otherwise healthy portion of tissue of a subject having an NLRP3-inflammasome inflammatory and/or degenerative disease.

The molecular mechanisms that control NLRP3 inflammasome are complex and include aberrant elements (Gross et al., 2011). Without being bound by theory, upon ligand (e.g., oxidized mtDNA) binding NLRP3 is thought to unfold and expose its pyrin domain, which binds to the adaptor protein ASC (apoptosis associated spike-like protein) that recruits the effector molecule pro-caspase-1 via CARD:CARD interactions to form a large cytosolic complex/aggregate—the NLRP3 inflammasome (Gross et al., 2011; Kotas and Medzhitov, 2015; Lu et al., 2014). Inflammasome assembly results in self cleavage and activation of caspase-1, which converts immature proinflammatory cytokines (e.g., pro-IL-1β and pro-IL-18) to their mature forms (Gross et al., 2011). Although DAMP-induced NLRP3 inflammasome activation is important for stimulation of tissue repair and regenerative processes (Karin and Clevers, 2016), aberrant NLRP3 activation appears to be the key to many chronic diseases, including cryopyrin-associated periodic syndromes, gout, Alzheimer's disease, type 2 diabetes, atherosclerosis, lupus, macular degeneration and cancer (Heneka et al., 2014; Lamkanfi and Dixit, 2012; Martinon et al., 2009). Heretofore, the ligand that binds to NLRP3 to induce inflammasome activation and IL-1β production has not been identified.

NLRP3 inflammasome activation and production of bioactive IL-1β require two functionally distinct steps: "priming" and "activation" (Gross et al., 2011; Zhong et al., 2016; Martinon et al., 2009). "Priming" entails direct engagement of Toll-like receptors (TLR) by PAMP and DAMP, such as LPS, resulting in rapid NF-κB activation, which leads to de novo synthesis of pro-IL-1β and upregulation of NLRP3 expression. The subsequent "activation" step is more mysterious, leading to NLRP3 inflammasome assembly and eventual caspase-1 self-cleavage and activation (Gross et al., 2011; Lu et al., 2014; Schroder and Tschopp, 2010). A major difficulty in understanding "activation" is the ability of numerous chemically and structurally diverse extracellular stimuli, often referred to as "NLRP3 agonists" or "NLRP3 activators", which include microparticles, microfibers, pore-forming toxins, ATP, and some pathogens, to trigger inflammasome assembly, although none of them directly binds NLRP3 (Gross et al., 2011; Latz et al., 2013). One solution to this conundrum is the proposal that all NLRP3 activators operate through a common intracellular intermediate, most likely the mitochondrion (Nakahira et al., 2011; Zhong et al., 2016; Zhou et al., 2011). Engaging different mechanisms, some of which involve plasma membrane damage, $K^+$ efflux and elevated intracellular $Ca^{2+}$, NLRP3 activators elicit a particular form of mitochondrial damage that causes release of fragmented mitochondrial (mt) DNA and increased production of reactive oxygen species (ROS) that convert mtDNA to an oxidized form, Ox-mtDNA, which was suggested to serve as a direct NLRP3 ligand (Shimada et al., 2012). The type of mitochondrial damage induced by NLRP3 agonists is distinct from that induced by pro-apoptotic members of the BCL2 family, which enable cytochrome c release and activation of the APAF complex that culminate in caspase-3, rather than caspase-1, activation (Jiang and Wang, 2004).

In contrast to the other known inflammasomes, activation of the NLRP3 inflammasome can be achieved by a wide range of structurally dissimilar stimuli, including pathogens, pore-forming toxins, environmental irritants, and endogenous DAMPs (Gross et al., 2011). Numerous molecules may trigger the formation and activation of the NLRP3 inflammasome.

By blocking the increase in NLRP3 inflammasome activation and production, the present disclosure demonstrates the ability to prevent such diseases associated with aberrant or persistent NLRP3 inflammasome activation and production. Accordingly, in one aspect, the invention provides a method of treating NLRP3 inflammasome-associated inflammatory and/or degenerative diseases in a subject in need thereof. The method includes administering to the subject an effective amount of an inhibitor of NLRP3 inflammasome activation. In various embodiments, the inhibitor of NLRP3 inflammasome activation may be an inhibitor of interferon regulatory factor 1 (IRF1) activity or expression and/or cytidine monophosphate kinase 2 (CMPK2) activity or expression. In various embodiments, the inhibitor of CMPK2 activity or expression is small molecule, peptide, antisense oligonucleotide, guide RNA, shRNA, antibody or an antibody fragment.

In various embodiments, the inhibitor of CMPK2 activity or expression is an inhibitory nucleic acid that specifically inhibits expression of CMPK2 and/or inhibits CMPK2 activation. As used herein, an "inhibitory nucleic acid" means an RNA, DNA, or a combination thereof that interferes or interrupts the translation of mRNA. Inhibitory nucleic acids can be single or double stranded. The nucleotides of the inhibitory nucleic acid can be chemically modified, natural or artificial. The terms "short-inhibitory RNA" and "siRNA" interchangeably refer to short double-stranded RNA oligonucleotides that mediate RNA interference (also referred to as "RNA-mediated interference" or "RNAi"). The terms "small hairpin RNA" and "shRNA" interchangeably refer to an artificial RNA molecule with a tight hairpin turn that can be used to silence target gene expression via RNAi. RNAi is a highly conserved gene silencing event functioning through targeted destruction of individual mRNA by a homologous double-stranded small interfering RNA (siRNA) (Fire, A. et al., Nature 391:806-811 (1998)). Mechanisms for RNAi are reviewed, for example, in Bayne and Allshire, Trends in Genetics (2005) 21:370-73; Morris, Cell Mol Life Sci (2005) 62:3057-66; Filipowicz, et al., Current Opinion in Structural Biology (2005) 15:331-41.

Methods for the design of siRNA or shRNA target sequences have been described in the art. Among the factors to be considered include: siRNA target sequences should be specific to the gene of interest and have about 20-50% GC content (Henshel et al., Nucl. Acids Res., 32: 113-20 (2004); G/C at the 5' end of the sense strand; A/U at the 5' end of the antisense strand; at least 5 A/U residues in the first 7 bases of the 5' terminal of the antisense strand; and no runs of more than 9 G/C residues (Ui-Tei et al., Nucl. Acids Res., 3: 936-48 (2004)). Additionally, primer design rules specific to the RNA polymerase will apply. For example, for RNA polymerase III, the polymerase that transcribes from the U6 promoter, the preferred target sequence is 5'-GN18-3'. Runs of 4 or more Ts (or As on the other strand) will serve as terminator sequences for RNA polymerase III and should be avoided. In addition, regions with a run of any single base should be avoided (Czauderna et al., Nucl. Acids Res., 31: 2705-16 (2003)). It has also been generally recommended that the mRNA target site be at least 50-200 bases downstream of the start codon (Sui et al., Proc. Natl. Acad. Sci. USA, 99: 5515-20 (2002); Elbashir et al., Methods, 26: 199-213 (2002); Duxbury and Whang, J. Surg. Res., 117: 339-44 (2004) to avoid regions in which regulatory proteins might bind. Additionally, a number of computer programs are available to aid in the design of suitable siRNA and shRNAs for use in suppressing expression of casp2 and/or inhibiting casp2 synthesis.

Ribozymes that cleave mRNA at site-specific recognition sequences can be used to destroy target mRNAs, particularly through the use of hammerhead ribozymes. Hammerhead ribozymes cleave mRNAs at locations dictated by flanking regions that form complementary base pairs with the target mRNA. Preferably, the target mRNA has the following sequence of two bases: 5'-UG-3'. The construction and production of hammerhead ribozymes is well known in the art.

Gene targeting ribozymes may contain a hybridizing region complementary to two regions, each of at least 5 and preferably each 6, 7, 8, 9, 10, 11, 12, 13, 14, 15, 16, 17, 18, 19 or 20 contiguous nucleotides in length of a target mRNA. In addition, ribozymes possess highly specific endoribonuclease activity, which autocatalytically cleaves the target sense mRNA.

With regard to antisense, siRNA or ribozyme oligonucleotides, phosphorothioate oligonucleotides can be used. Modifications of the phosphodiester linkage as well as of the heterocycle or the sugar may provide an increase in efficiency. Phophorothioate is used to modify the phosphodiester linkage. An N3'-P5' phosphoramidate linkage has been described as stabilizing oligonucleotides to nucleases and increasing the binding to RNA. Peptide nucleic acid (PNA) linkage is a complete replacement of the ribose and phosphodiester backbone and is stable to nucleases, increases the binding affinity to RNA, and does not allow cleavage by RNAse H. Its basic structure is also amenable to modifications that may allow its optimization as an antisense component. With respect to modifications of the heterocycle, certain heterocycle modifications have proven to augment antisense effects without interfering with RNAse H activity. An example of such modification is C-5 thiazole modification. Finally, modification of the sugar may also be considered. 2'-O-propyl and 2'-methoxyethoxy ribose modifications stabilize oligonucleotides to nucleases in cell culture and in vivo.

CRISPR (Clustered Regularly Interspaced Short Palindromic Repeats) is an acronym for DNA loci that contain multiple, short, direct repetitions of base sequences. The prokaryotic CRISPR/Cas system has been adapted for use as gene editing (silencing, enhancing or changing specific genes) for use in eukaryotes (see, for example, Cong, Science, 15:339(6121):819-823 (2013) and Jinek, et al., Science, 337(6096):816-21 (2012)). By transfecting a cell with elements including a Cas gene and specifically designed CRISPRs, nucleic acid sequences can be cut and modified at any desired location. Methods of preparing compositions for use in genome editing using the CRISPR/Cas systems are described in detail in US Pub. No. 2016/0340661, US Pub. No. 20160340662, US Pub. No. 2016/0354487, US Pub. No. 2016/0355796, US Pub. No. 20160355797, and WO 2014/018423, which are specifically incorporated by reference herein in their entireties.

Thus, as used herein, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer", "guide RNA" or "gRNA" in the context of an endogenous CRISPR system), or other sequences and transcripts from a CRISPR locus. One or more tracr mate sequences operably linked to a guide sequence (e.g., direct repeat-spacer-direct repeat) can also be referred to as "pre-crRNA" (pre-CRISPR RNA) before processing or crRNA after processing by a nuclease.

There are many resources available for helping practitioners determine suitable target sites once a desired DNA target sequence is identified. For example, numerous public resources, including a bioinformatically generated list of about 190,000 potential sgRNAs, targeting more than 40% of human exons, are available to aid practitioners in selecting target sites and designing the associate sgRNA to affect a nick or double strand break at the site. See also, crispr.u-psud.fr, a tool designed to help scientists find CRISPR targeting sites in a wide range of species and generate the appropriate crRNA sequences.

Inhibitory nucleic acids, such as siRNA, shRNA, ribozymes, or antisense molecules, can be synthesized and introduced into cells using methods known in the art. Molecules can be synthesized chemically or enzymatically in vitro (Micura, Agnes Chem. Int. Ed. Emgl. 41 2265-9 (2002); Paddison et al., Proc. Natl. Acad. Sci. USA, 99:1443-8 2002) or endogenously expressed inside the cells in the form of shRNAs (Yu et al., Proc. Natl. Acad. Sci. USA, 99:6047-52 (2002); McManus et al., RNA 8, 842-50 (2002)). Plasmid-based expression systems using RNA polymerase III U6 or H1, or RNA polymerase II U1, small nuclear RNA promoters, have been used for endogenous expression of shRNAs (Brummelkamp et al., Science, 296: 550-3 (2002); Sui et al., Proc. Natl. Acad. Sci. USA, 99: 5515-20 (2002); Novarino et al., J. Neurosci., 24: 5322-30 (2004)). Synthetic siRNAs can be delivered by electroporation or by using lipophilic agents (McManus et al., RNA 8, 842-50 (2002); Kishida et al., J. Gene Med., 6: 105-10 (2004)). Alternatively, plasmid systems can be used to stably express small hairpin RNAs (shRNA) for the suppression of target genes (Dykxhoorn et al., Nat. Rev. Mol. Biol., 4:457-67 (2003)). Various viral delivery systems have been developed to deliver shRNA-expressing cassettes into cells that are difficult to transfect (Brummelkamp et al., Cancer Cell, 2: 243-7 (2002); Rubinson et al., Nat. Genet., 33: 401-6 2003). Furthermore, siRNAs can also be delivered into live animals. (Hasuwa et al., FEBS Lett., 532, 227-30 (2002); Carmell et al., Nat. Struct. Biol., 10: 91-2 (2003); Kobayashi et al., J. Pharmacol. Exp. Ther., 308:688-93 (2004)).

Inhibitory oligonucleotides can be delivered to a cell by direct transfection or transfection and expression via an expression vector. Appropriate expression vectors include mammalian expression vectors and viral vectors, into which has been cloned an inhibitory oligonucleotide with the appropriate regulatory sequences including a promoter to result in expression of the antisense RNA in a host cell. Suitable promoters can be constitutive or development-specific promoters. Transfection delivery can be achieved by liposomal transfection reagents, known in the art (e.g., Xtreme transfection reagent, Roche, Alameda, Calif.; Lipofectamine formulations, Invitrogen, Carlsbad, Calif.). Delivery mediated by cationic liposomes, by retroviral vectors and direct delivery are efficient. Another possible delivery mode is targeting using antibody to cell surface markers for the target cells.

In some embodiments, one or more vectors driving expression of one or more elements of a CRISPR system are introduced into a target cell such that expression of the elements of the CRISPR system direct formation of a CRISPR complex at one or more target sites. Accordingly, cleavage of DNA by the genome editing vector or composition can be used to delete nucleic acid material from a target DNA sequence by cleaving the target DNA sequence and allowing the cell to repair the sequence. As such, the compositions can be used to modify DNA in a site-specific, i.e., "targeted" way, for example gene knock-out, gene knock-in, gene editing, gene tagging, etc., as used in, for example, gene therapy.

While the specifics can be varied in different engineered CRISPR systems, the overall methodology is similar. A practitioner interested in using CRISPR technology to target a DNA sequence can insert a short DNA fragment containing the target sequence into a guide RNA expression plasmid. The sgRNA expression plasmid contains the target sequence (about 20 nucleotides), a form of the tracrRNA sequence (the scaffold) as well as a suitable promoter and necessary elements for proper processing in eukaryotic cells. Such vectors are commercially available (see, for example, Addgene). Many of the systems rely on custom, complementary oligos that are annealed to form a double stranded DNA and then cloned into the sgRNA expression plasmid. Co-expression of the sgRNA and the appropriate Cas enzyme from the same or separate plasmids in transfected cells results in a single or double strand break (depending of the activity of the Cas enzyme) at the desired target site.

In another aspect, the present invention provides a method of ameliorating NLRP3 inflammasome-associated inflammatory and/or degenerative diseases in a subject. As used herein, the term "ameliorate" means that the clinical signs and/or the symptoms associated with NLRP3 inflammasome-associated inflammatory and/or degenerative diseases are lessened. The signs or symptoms to be monitored will be characteristic of a particular disease or disorder and will be well known to the skilled clinician, as will the methods for monitoring the signs and conditions thereof.

In another aspect, the present invention provides a method of identifying an agent useful for treating a NLRP3 inflammasome-associated inflammatory and/or degenerative disease or disorder through the targeting of IRF1 and/or CMPK2. The method includes contacting a sample of cells with at least one test agent, wherein a decrease in NLPR3 inflammasome activation in the presence of the test agent as compared to NLPR3 inflammasome activation in the absence of the test agent identifies the agent as useful for treating NLRP3 inflammasome-associated inflammatory and degenerative diseases. In one embodiment, a decrease in IRF1 activity or expression and/or a decrease in CMPK2 activity or expression in the presence of the test agent as compared to IRF1 activity or expression and/or CMPK2 activity or expression in the absence of the test agent identifies the agent as useful for treating a NLRP3 inflammasome-associated inflammatory and degenerative disease. In various embodiments, the method may be performed in a high throughput format, such as contacting samples of cells of a plurality of samples with at least one test agent. In various embodiments, the plurality of samples may be obtained from a single subject or from different subjects.

An agent useful in a method of the invention can be any type of molecule, for example, a polynucleotide, a peptide, antisense oligonucleotide, antibody or antibody fragment, a peptidomimetic, peptoids such as vinylogous peptoids, a small organic molecule, a nucleotide analog, or the like, and can act in any of various ways to reduce or inhibit elevated NLPR3 inflammasome activation, IRF1 activity or expression, and/or CMPK2 activity or expression. In various embodiments, the inhibitor of inhibitor of CMPK2 activity or expression is an inhibitory nucleic acid that inhibits the expression of CMPK2. For example, the inhibitory nucleic acid can be siRNA, shRNA, guide RNA (gRNA), oligonucleotides, antisense RNA or ribozymes that inhibit CMPK2 synthesis.

Further, the agent can be administered in any way typical of an agent used to treat the particular type of above-mentioned diseases or under conditions that facilitate contact of the agent with the target diseased cells and, if appropriate, entry into the cells. Entry of a polynucleotide agent into a cell, for example, can be facilitated by incorporating the polynucleotide into a viral vector that can infect the cells. Thus, the inhibitory nucleic acid can be delivered in, for example, a lentiviral vector, a herpesvirus vector or an adenoviral vector.

If a viral vector specific for the cell type is not available, the vector can be modified to express a receptor (or ligand) specific for a ligand (or receptor) expressed on the target cell, or can be encapsulated within a liposome, which also can be modified to include such a ligand (or receptor). A peptide agent can be introduced into a cell by various methods, including, for example, by engineering the peptide to contain a protein transduction domain such as the human immunodeficiency virus TAT protein transduction domain, which can facilitate translocation of the peptide into the cell.

Generally, the agent is formulated in a composition (e.g., a pharmaceutical composition) suitable for administration to the subject, which can be any vertebrate subject, including a mammalian subject (e.g., a human subject). Such formulated agents are useful as medicaments for treating a subject suffering from any of the above-mentioned diseases, in part, by elevated or abnormally elevated NLRP3 inflammasome activation.

Pharmaceutically acceptable carriers useful for formulating an agent for administration to a subject are well known in the art and include, for example, aqueous solutions such as water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the physico-chemical characteristics of the therapeutic agent and on the route of administration of the composition, which can be, for example, orally or parenterally such as intravenously, and by injection, intubation, or other such method known in the art. The pharmaceutical composition also can contain a second (or more) compound(s) such as a diagnostic reagent, nutritional substance, toxin, or therapeutic agent, for example, a cancer chemotherapeutic agent and/or vitamin(s).

In general, a suitable daily dose of a compound/inhibitor of the invention will be that amount of the compound/inhibitor that is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day which can be administered in single or multiple doses.

When practiced as an in vitro assay, the methods can be adapted to a high throughput format, thus allowing the examination of a plurality (i.e., 2, 3, 4, or more) of cell samples and/or test agents, which independently can be the same or different, in parallel. A high throughput format provides numerous advantages, including that test agents can be tested on several samples of cells from a single patient, thus allowing, for example, for the identification of a particularly effective concentration of an agent to be administered to the subject, or for the identification of a particularly effective agent to be administered to the subject. As such, a high throughput format allows for the examination of two, three, four, etc., different test agents, alone or in combination, on the macrophages of a subject such that the best (most effective) agent or combination of agents can be used for a therapeutic procedure. Further, a high throughput format allows, for example, control samples (positive controls and or negative controls) to be run in parallel with test samples, including, for example, samples of cells known to be effectively treated with an agent being tested.

A high throughput method of the invention can be practiced in any of a variety of ways. For example, different samples of cells obtained from different subjects can be examined, in parallel, with same or different amounts of one or a plurality of test agent(s); or two or more samples of cells obtained from one subject can be examined with same or different amounts of one or a plurality of test agent. In addition, cell samples, which can be of the same or different subjects, can be examined using combinations of test agents and/or known effective agents. Variations of these exemplified formats also can be used to identify an agent or combination of agents useful for treating any of the above-mentioned diseases associated with NLRP3 inflammasome activation.

When performed in a high throughput (or ultra-high throughput) format, the method can be performed on a solid support (e.g., a microtiter plate, a silicon wafer, or a glass slide), wherein samples to be contacted with a test agent are positioned such that each is delineated from each other (e.g., in wells). Any number of samples (e.g., 96, 1024, 10,000, 100,000, or more) can be examined in parallel using such a method, depending on the particular support used. Where samples are positioned in an array (i.e., a defined pattern), each sample in the array can be defined by its position (e.g., using an x-y axis), thus providing an "address" for each sample. An advantage of using an addressable array format is that the method can be automated, in whole or in part, such that cell samples, reagents, test agents, and the like, can be dispensed to (or removed from) specified positions at desired times, and samples (or aliquots) can be monitored, for example, for NLRP3 inflammasome activation and/or cell viability.

The invention also provides a method of determining whether any of the above-mentioned NLRP3 inflammasome-associated inflammatory and degenerative disease or disorder is amenable to treatment with an inhibitor of NLRP3 inflammasome activation, as disclosed herein. The method can be performed, for example, by measuring the amount of NLRP3 inflammasome activation, the level of expression or activity of IRF1, and/or the level of expression or activity of CMPK2 in a cell sample of a subject to be treated, and determining that the measured NLRP3 inflammasome activation, expression or activity of IRF1, and/or expression or activity of CMPK2 is elevated or abnormally elevated as compared to the level of NLRP3 inflammasome activation, expression or activity of IRF1, and/or expression or activity of CMPK2 in corresponding normal cells, which can be a sample of normal (i.e., not diseased) cells of the subject having any one of the above-mentioned inflammatory and/or degenerative diseases. Detection of elevated or abnormally elevated level of NLRP3 inflammasome activation expression or activity of IRF1, and/or expression or activity of CMPK2 in the cells as compared to the corresponding normal cells indicates that the subject can benefit from treatment with an inhibitor of NLRP3 inflammasome activation. A sample of cells used in the present method can be obtained using a biopsy procedure (e.g., a needle biopsy), or can be a sample of cells obtained by a surgical procedure to remove and/or debulk the tumor.

In various embodiments, the method of identifying a disease or disorder amenable to treatment with an inhibitor of NLRP3 inflammasome activation can further include contacting cells of the sample with at least one test agent known to inhibit NLRP3 inflammasome activation, IRF1 expression or activity, and/or CMPK2 expression or activity, and detecting a decrease in NLRP3 inflammasome activation or IL-1β release in the cells following said contact. Such a method provides a means to confirm that any of the above-mentioned diseases or disorders is amenable to treatment with an inhibitor of NLRP3 inflammasome activation. Further, the method can include testing one or more different test agents, either alone or in combination, thus providing a means to identify one or more test agents useful for treating the particular symptoms of any of the above-mentioned diseases or disorders being examined. Accordingly, the present invention provides a method of identifying an agent useful for treating lupus, gout, osteoarthritis, rheumatoid arthritis, ankylosing spondylitis, uveitis, Alzheimer's disease, Parkinson's disease, cryopyrin-associated periodic syndromes, type 2 diabetes, atherosclerosis, macular degeneration, lung cancer, and many more inflammatory and degenerative diseases in a subject.

Amino acid sequences and nucleic acid sequences for human cytidine monophosphate kinase 2 (CMPK2) and human interferon regulatory factor (IFR1) are known in the art. See, for example, Accession No.: Q5EMB0, human CMPK2, Isoform 1, which provides the amino acid sequence (SEQ ID NO: 1):

MAFARRLLRGPLSGPLLGRRGVCAGAMAPPRRFVLELPDCTLAHFALGAD

APGDADAPDPRLAALLGPPERSYSLCVPVTPDAGCGARVRAARLHQRLLH

QLRRGPFQRCQLLRLLCYCPGGQAGGAQQGFLLRDPLDDPDTRQALLELL

GACQEAPRPHLGEFEADPRGQLWQRLWEVQDGRRLQVGCAQVVPVPEPPL

HPVVPDLPSSVVFPDREAARAVLEECTSFIPEARAVLDLVDQCPKQIQKG

KFQVVAIEGLDATGKTTVTQSVADSLKAVLLKSPPSCIGQWRKIFDDEPT

IIRRAFYSLGNYIVASEIAKESAKSPVIVDRYWHSTATYAIATEVSGGLQ

HLPPAHHPVYQWPEDLLKPDLILLLTVSPEERLQRLQGRGMEKTREEAEL

EANSVFRQKVEMSYQRMENPGCHVVDASPSREKVLQTVLSLIQNSFSEP

Accession No.: P10914, human interferon regulatory factor (IFR1), which provides the amino acid effluence (SEQ ID NO: 2):

MPITRMRMRPWLEMQINSNQIPGLIWINKEEMIFQIPWKHAAKHGWDINK

DACLFRSWAIHTGRYKAGEKEPDPKTWKANFRCAMNSLPDIEEVKDQSRN

KGSSAVRVYRMLPPLTKNQRKERKSKSSRDAKSKAKRKSCGDSSPDTFSD

GLSSSTLPDDHSSYTVPGYMQDLEVEQALTPALSPCAVSSTLPDWHIPVE

VVPDSTSDLYNFQVSPMPSTSEATTDEDEEGKLPEDIMKLLEQSEWQPTN

VDGKGYLLNEPGVQPTSVYGDFSCKEEPEIDSPGGDIGLSLQRVFTDLKN

MDATWLDSLLTPVRLPSIQAIPCAP

The following examples are intended to illustrate but not limit the invention.

Example 1

LPS Induces TRIF-Dependent mtDNA Replication in Macrophages

Figure 6E:
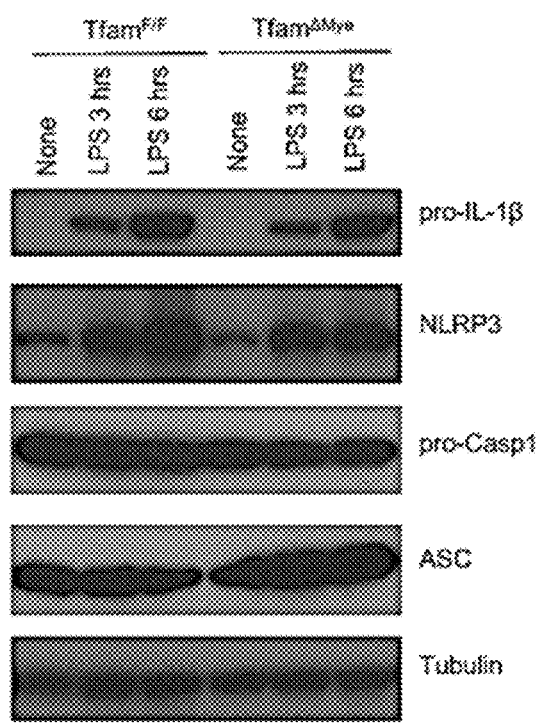
Figure 6F:
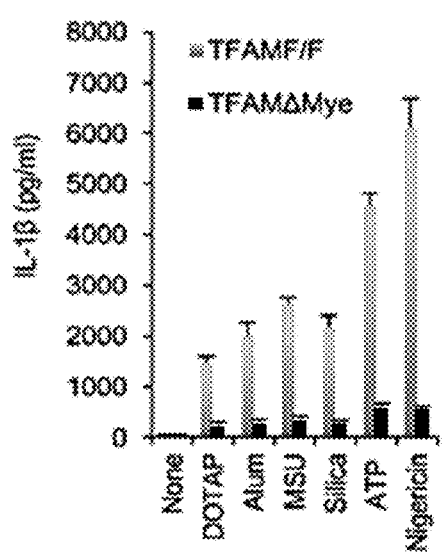
Figure 6G:
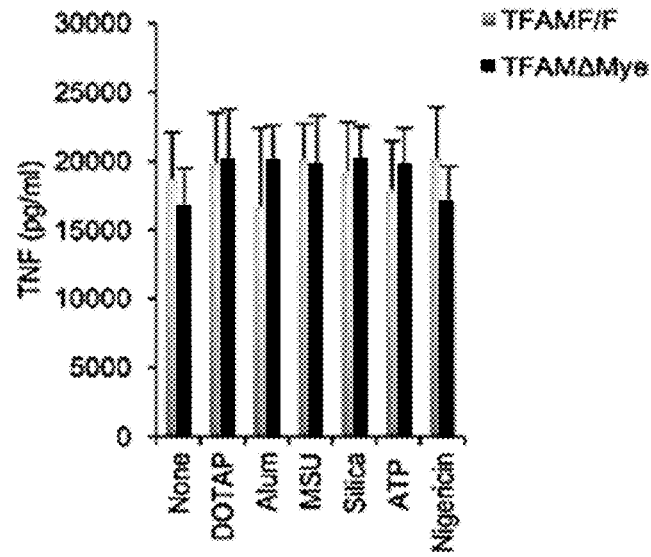

To demonstrate a role for mitochondria in NLRP3 inflammasome activation, it was decided to use low dose ethidium bromide (EtBr) to deplete cells of mtDNA (Nakahira et al., 2011; Zhong et al., 2016; Shimada et al., 2010). To firmly establish the role of mtDNA in NLRP3 inflammasome activation using a genetic approach, it was decided to cross $Tfam^{F/F}$ mice[16] with LysM-Cre mice to generate $Tfam^{\Delta Mye}$ mice, which specifically lack TFAM (transcription factor A, mitochondrial), a protein that binds mtDNA to promote its compaction and stabilization as well as replication and transcription (Kang et al. 2007), in mature myeloid cells. Tfam ablation dramatically reduced mtDNA copy number in bone marrow-derived macrophages (BMDM) (FIG. 6A and FIG. 6B). TFAM-deficient macrophages also failed to produce Ox-mtDNA in response to treatment with NLRP3 inflammasome activators and displayed defective caspase-1 activation and IL-1β processing, whilst retaining expression of pro-IL-1β and NLRP3 inflammasome components, normal AIM2 inflammasome activation in response to poly(dA:dT) and unaltered TNF expression (FIGS. 6C-6G). To rule out the possibility that TFAM itself rather than mtDNA is required for NLRP3 inflammasome activation, a D-loop (origin of replication) containing fragment of mouse mtDNA was amplified in the presence of the oxidized nucleotide 8-OH-dGTP to generate Ox-mtDNA. Transfection of this Ox-mtDNA into $Tfam^{\Delta Mye}$ BMDM restored LPS-induced IL-1β production (FIG. 1A). The effect was NLRP3 dependent, thus demonstrating that TFAM promotes NLRP3 inflammasome activation by facilitating Ox-mtDNA formation or release. Last but not least, it was confirmed that Ox-mtDNA indeed associated with inflammasome aggregates upon treatment with NLRP2 inflammasome activators (FIG. 6H).

Figure 1B:
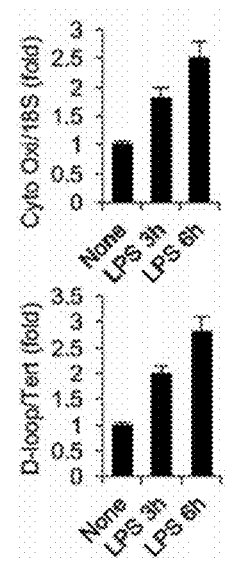
Figure 1C:
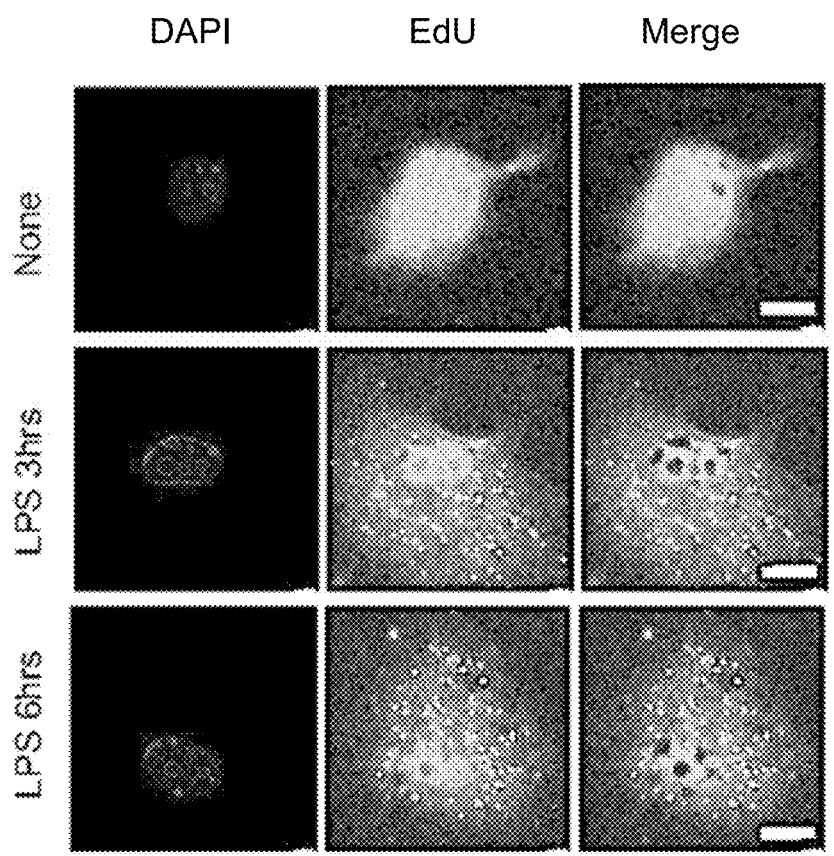
Figure 1D:
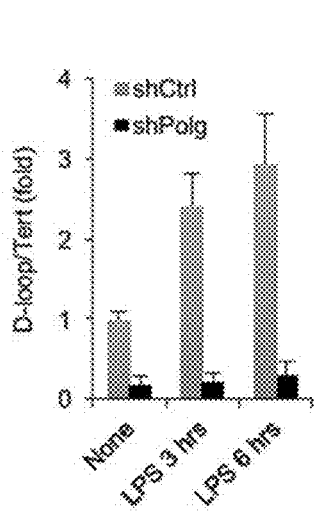
Figure 1E:
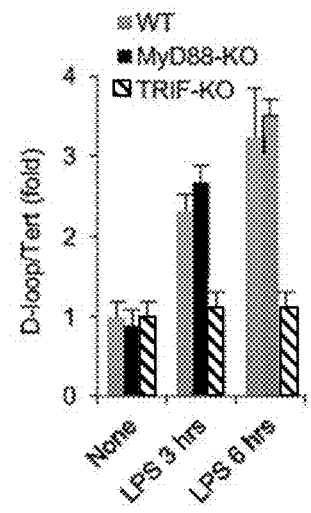
Figure 1F:
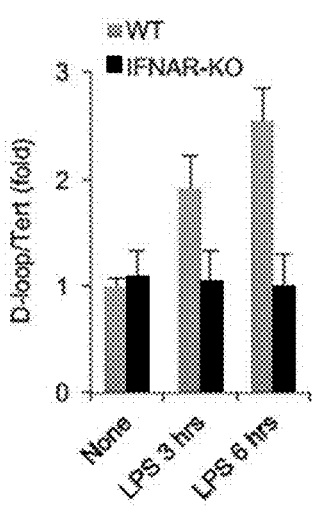

Since TFAM is required for mtDNA replication and maintenance, whether LPS-induced "priming" or stimulation with NLRP3 inflammasome activators affected mtDNA abundance was examined. Surprisingly, macrophage stimulation with LPS resulted in a rather rapid increase in mtDNA copy number (FIG. 1B), correlating with induction of EdU (5-ethynyl-2'-deoxyuridine) incorporation into cytoplasmic organelles (FIG. 1C). LPS-enhanced mtDNA replication was prevented by ablation of the Polg gene, which encodes DNA polymerase γ (Hudson, G. and Chinnery, P. F., 2006), the enzyme responsible for mtDNA replication (FIG. 1D). Since LPS binds TLR4, which signals via the adaptor proteins MyD88 and TRIF (Kawai, T. and Akira, S. 2010), it was decided to test their involvement in LPS-induced mtDNA replication. Ablation of TRIF prevented LPS-induced mtDNA replication (FIG. 1E). Ablation of MyD88 had a smaller effect, mainly at earlier time points. Ablation of both TRIF and MyD88 resulted in complete inhibition of LPS-stimulated mtDNA synthesis.

Example 2

IRF1 Controls mtDNA Replication and NLPR3 Inflammasome Activation

Figure 2A:
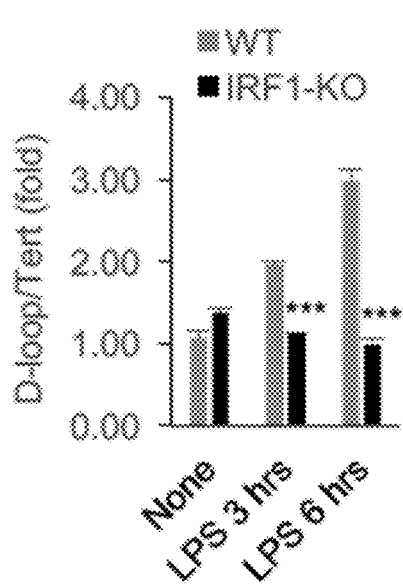
Figure 2B:
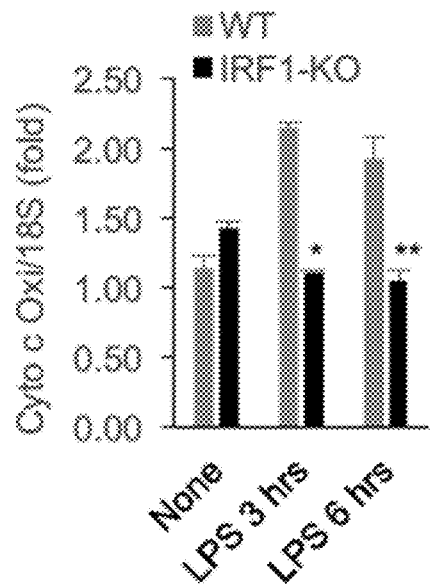
Figure 2C:
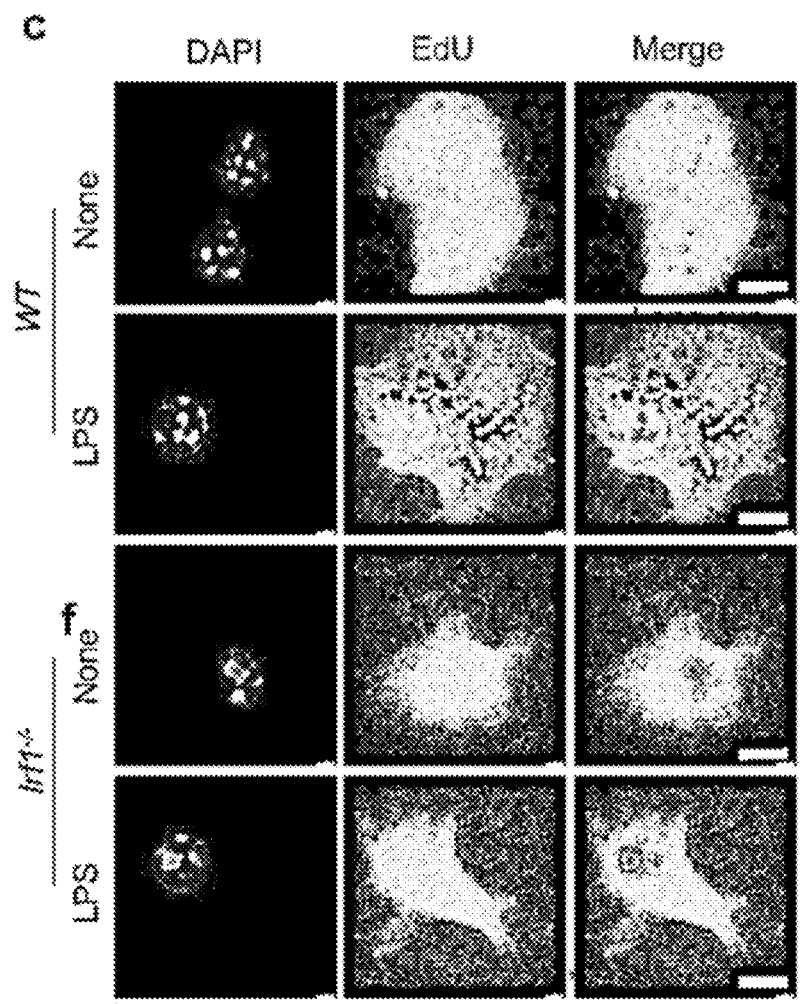
Figure 2D:
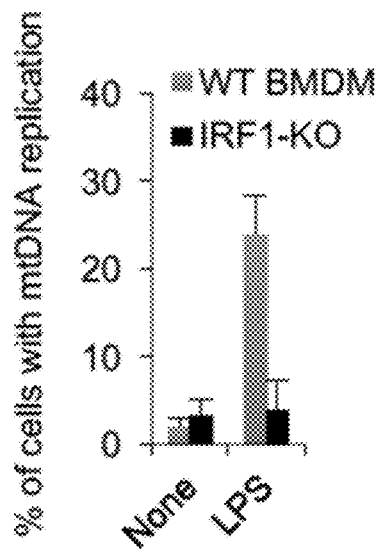
Figure 2E:
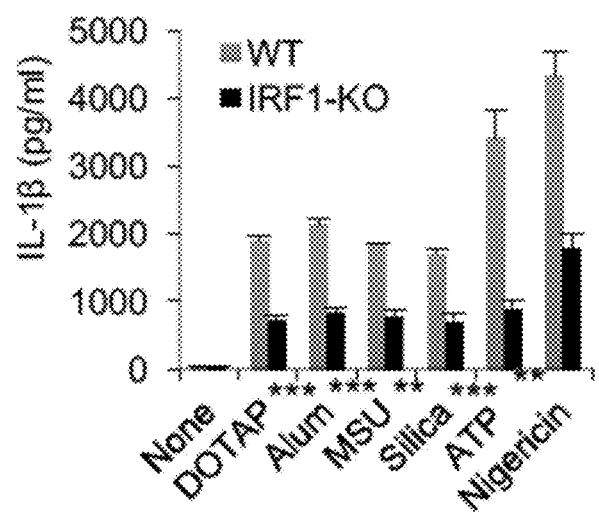
Figure 7C:
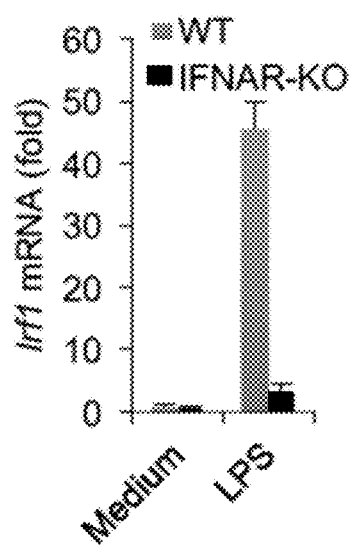
Figure 7D:
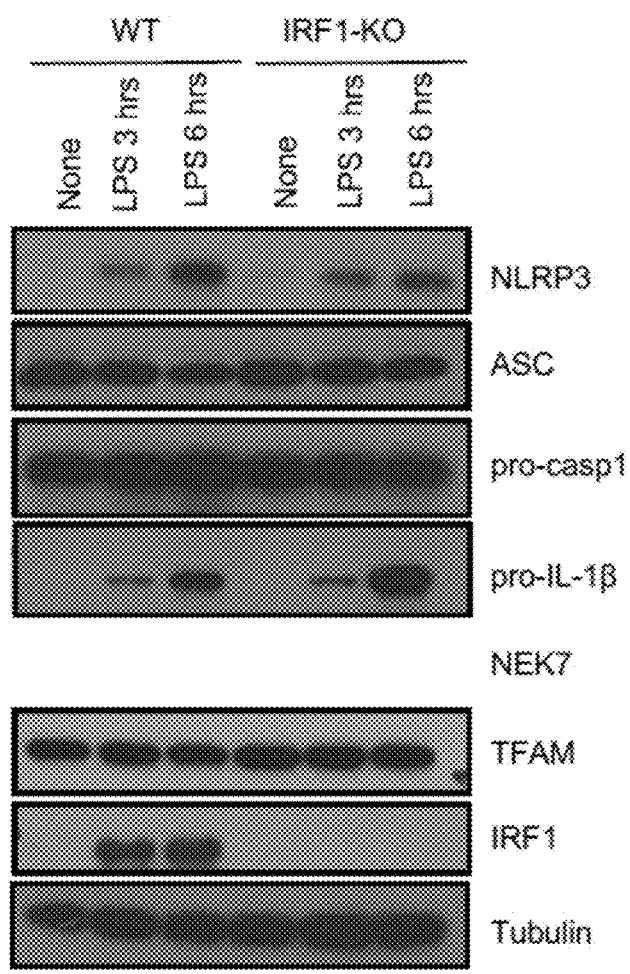
Figure 7E:
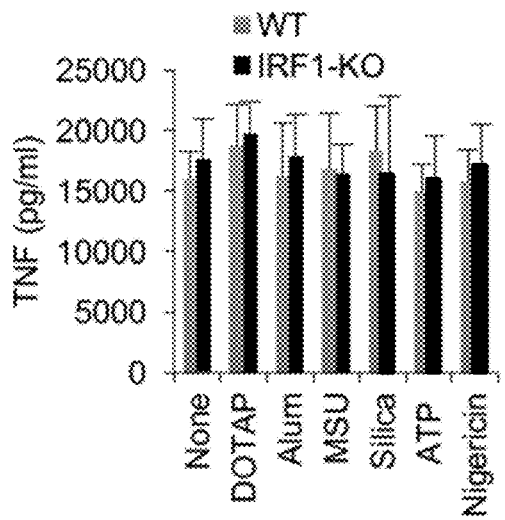
Figure 7F:
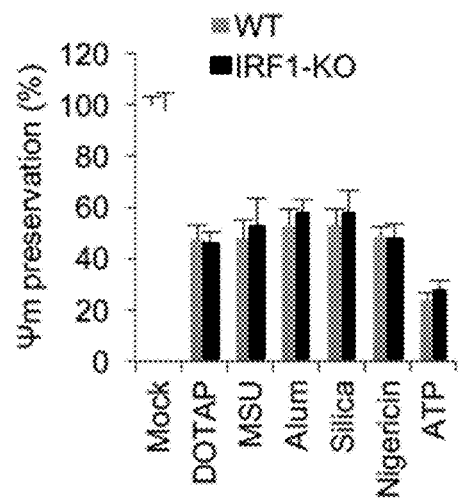
Figure 7G:
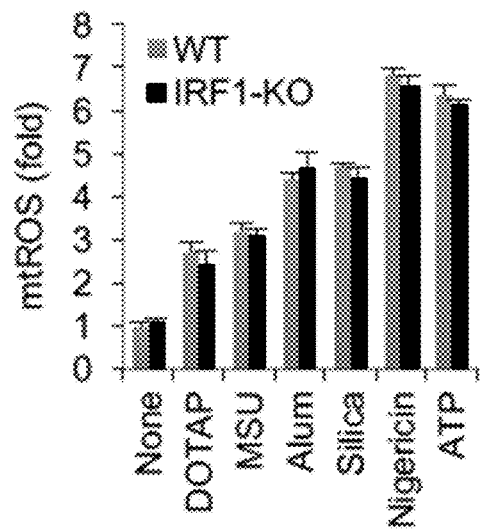

To identify how TLR signaling controls LPS-induced mtDNA replication, it was decided to examine members of the interferon regulatory factor (IRF) family and found that a deficiency in IRF1 obliterated LPS-induced mtDNA replication (FIGS. 2A-2D). Although resting macrophages barely expressed IRF1, LPS stimulation resulted in robust IRF1 mRNA and protein induction (FIGS. 7A-7C). IRF1 was also needed for NLRP3 inflammasome activation, with $Irf1^{-/-}$ BMDM showing a substantial (50~70%) reduction in "NLRP3 agonist"-induced caspase-1 activation and IL-1β release, without an effect on AIM2 inflammasome activation (FIGS. 2E and 2F). Expression of NLRP3 inflammasome components and pro-IL-1β and TNF secretion were also unaffected by IRF1 ablation, which also had no effect on NLRP3 agonist-induced mitochondrial damage or mtROS production (FIG. 7D-7G), but due to defective LPS-induced mtDNA replication, less Ox-mtDNA was found in $Irf1^{-/-}$ BMDM after "NLRP3 agonist" stimulation (FIG. 2G). These observations suggest that IRF1 controls Ox-mtDNA production and NLRP3 inflammasome activation through its effect on mtDNA replication.

Example 3

CMPK2 Controls mtDNA Replication and NLRP3 Inflammasome Activation

Figure 8A:
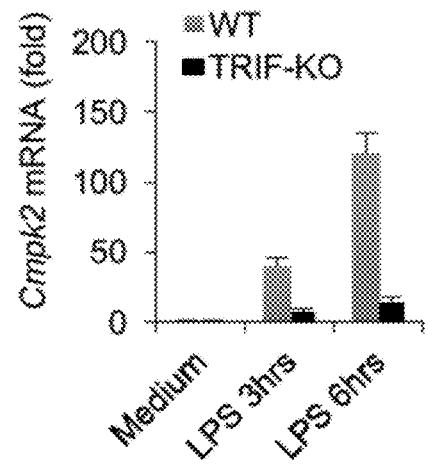
FIGS. 8A-8D are pictorial and graphical diagrams showing that LPS-induced CMPK2 expression depends on the signaling proteins TRIF and IFNAR.
Figure 8B:
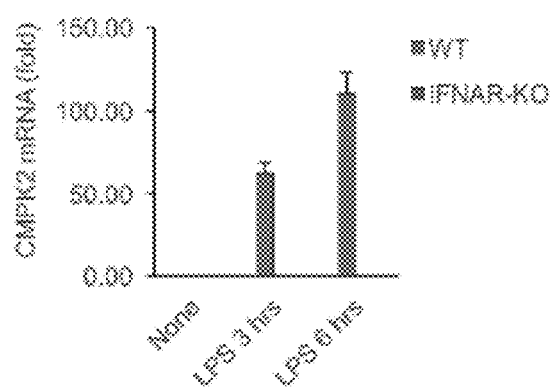
Figure 8C:
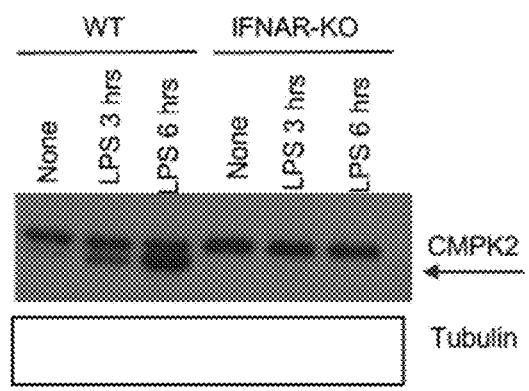
Figure 8D:
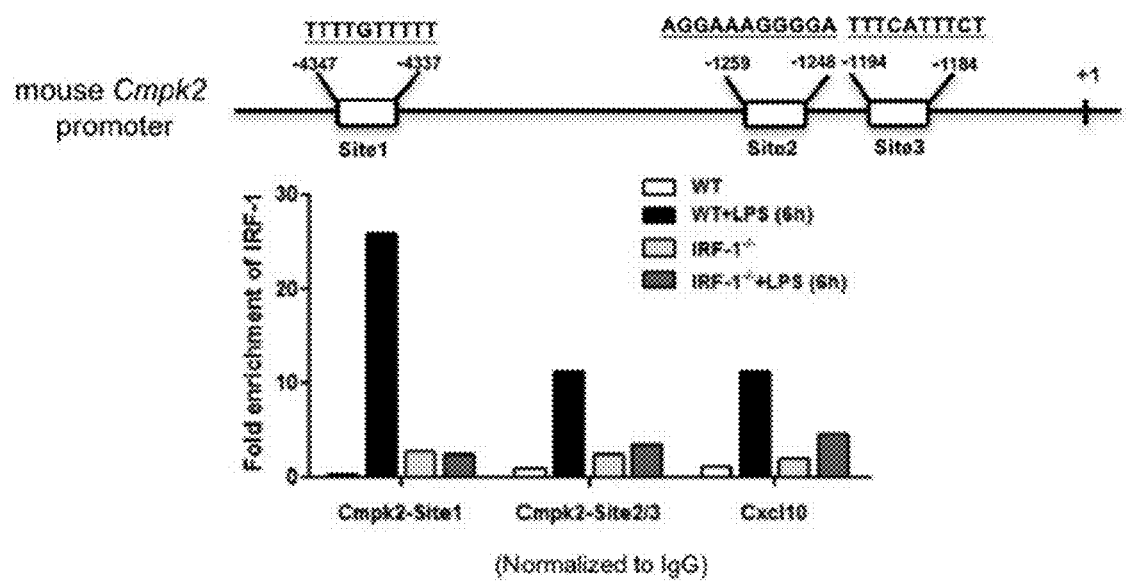
Figure 9:
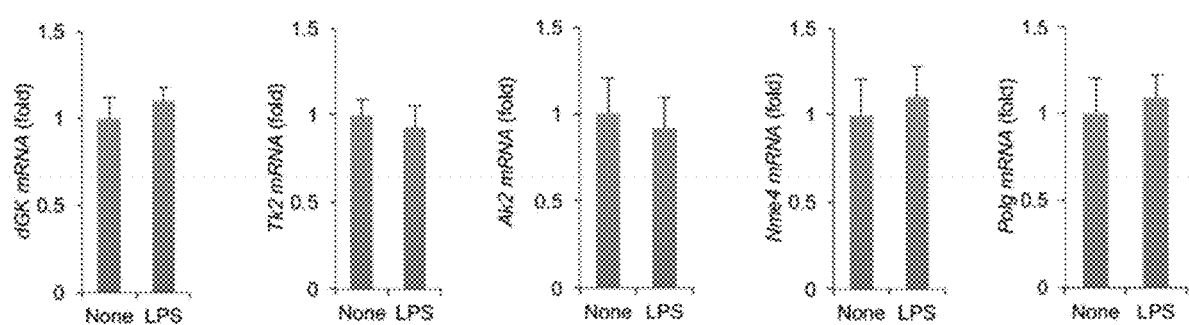
FIG. 9 is a series of graphical diagrams showing that expression of mitochondrial dNTP salvage pathway enzymes and DNA polymerase γ.

Since IRF1 is a transcription factor, it was decided to investigate whether any of its previously described target genes may be involved in mtDNA replication and found that the IRF1 transcriptome (Jehl et al., 2010) included the gene coding for UMP-CMPK2 (hereafter referred to as "CMPK2"), a mitochondrial deoxyribonucleotide kinase (Ullah et al., 2012). Of note, LPS priming resulted in strong induction of CMPK2 mRNA and protein, whose expression was barely detectable in resting macrophages (FIG. 3A and FIG. 3B). Importantly, LPS-induced CMPK2 upregulation was IRF1 dependent, and Trif$^{-/-}$ and Ifnar1$^{-/-}$ BMDM also failed to upregulate CMPK2 upon LPS priming (FIGS. 8A-8C). The Cmpk2 promoter contained IRF1 binding sites. CMPK2 is a mitochondria-resident nucleotide kinase that is part of the salvage pathway for mitochondrial dNTP synthesis (Xu et al., 2008). Intriguingly, other nucleoside/nucleotide kinases in this pathway and Polγ were not LPS-inducible (FIG. 9), suggesting that CMPK2 is the rate-limiting enzyme that controls the supply of dNTP precursors for LPS-induced mtDNA synthesis. CMPK2 phosphorylates dCMP to generate dCDP, which is further converted into dCTP by the mitochondrial deoxyribonucleotide kinase NME4 (Xu et al., 2008; Milon et al., 2000). Unlike CMPK2, NME4 was expressed constitutively and was not LPS responsive.

Figure 10A:
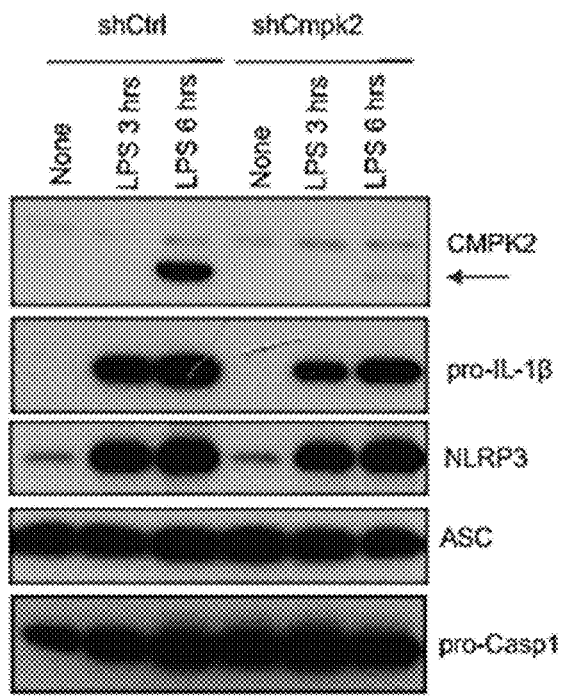
FIGS. 10A-10C are pictorial and graphical diagrams showing that CMPK2 does not affect inflammasome subunit expression and NLRP3 agonist-induced mitochondrial damage.
Figure 10B:
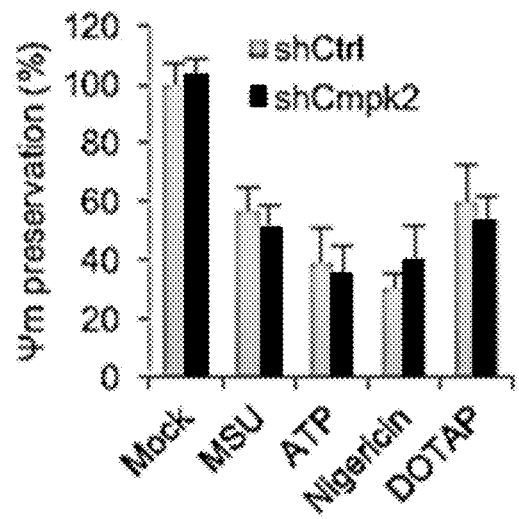
Figure 10C:
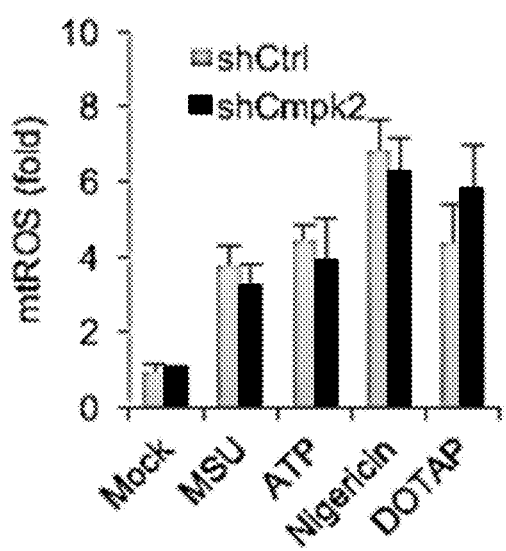

To test the role of CMPK2 in mtDNA replication and NLRP3 inflammasome activation, we knocked down Cmpk2 using shRNA. CMPK2-deficient macrophages (shCmpk2 BMDM) exhibited minimal NLRP3 inflammasome activator-induced caspase-1 activation and IL-1β maturation in comparison with CMPK2-sufficient cells (shCtrl), while retaining normal AIM2 inflammasome activation (FIG. 3C and FIG. 3D). Expression of NLRP3 inflammasome components and pro-IL-1β was unaffected (FIG. 10A). Although CMPK2 ablation did not affect the extent of mitochondrial damage or mtROS production after exposure to NLRP3 inflammasome activators (FIG. 10B and FIG. 10C), shCmpk2 BMDM failed to upregulate mtDNA replication after LPS stimulation and barely produced Ox-mtDNA (FIG. 3E and FIG. 3F).

Figure 11A:
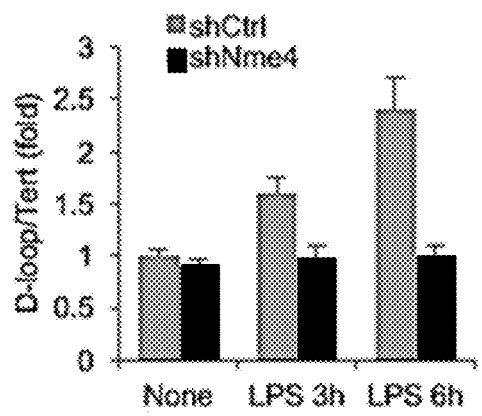
FIGS. 11A-11D are graphical diagrams showing that NME4 is needed for NLRP3 inflammasome activation.
Figure 11B:
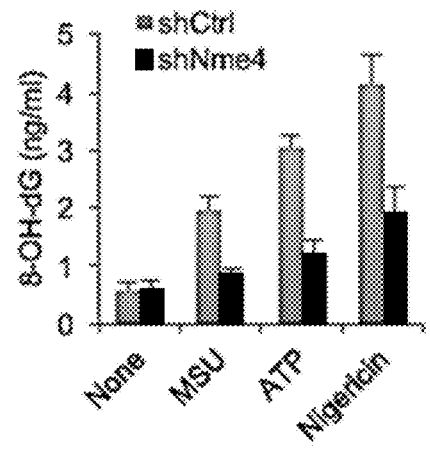
Figure 11C:
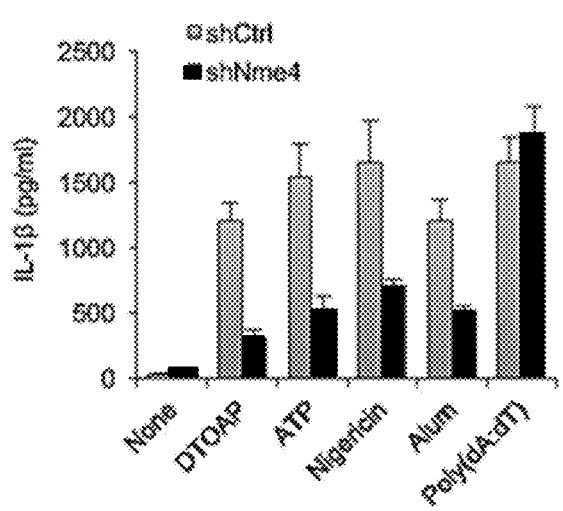
Figure 11D:
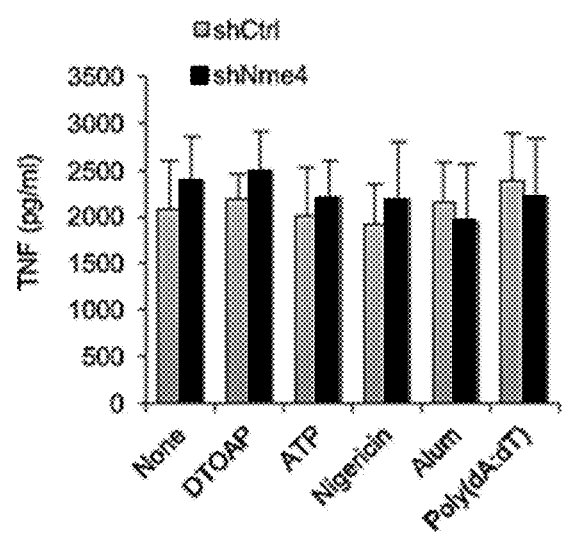

To test whether inactivation of other components of the mitochondrial nucleotide salvage pathway also inhibits NLRP3 inflammasome activation, we knocked down Nme4. shNme4 BMDM failed to replicate mtDNA after LPS priming, exhibited much lower Ox-mtDNA production than WT BMDM and consequently secreted much less IL-1β after stimulation with NLRP3 inflammasome activators (FIGS. 11A-11C). NME4 silencing, however, did not affect AIM2 inflammasome activation nor LPS-induced TNF production and did not diminish CMPK2 induction (FIGS. 11C and 11D).

Example 4

Figure 4A:
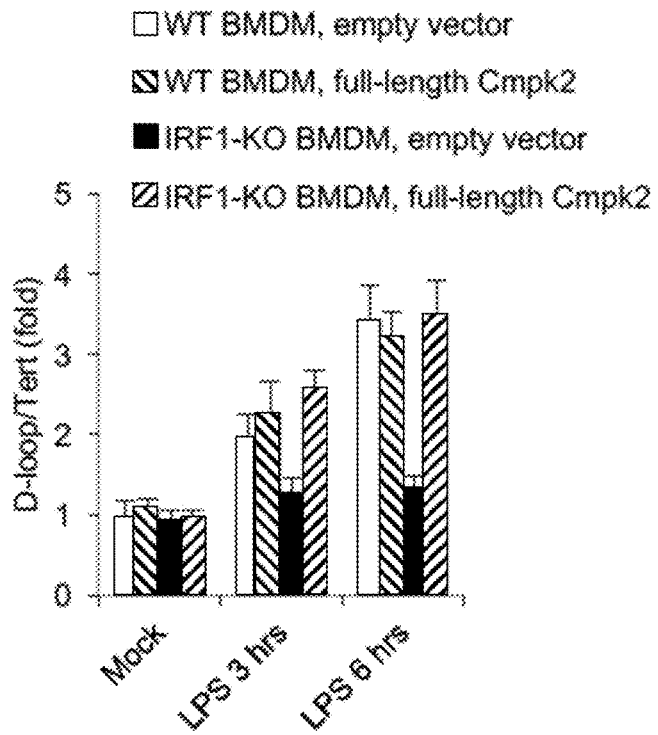
FIGS. 4A-4D are graphical diagrams showing CMPK2 catalytic activity is required for IRF1-dependent NLRP3 inflammasome activation.
Figure 4B:
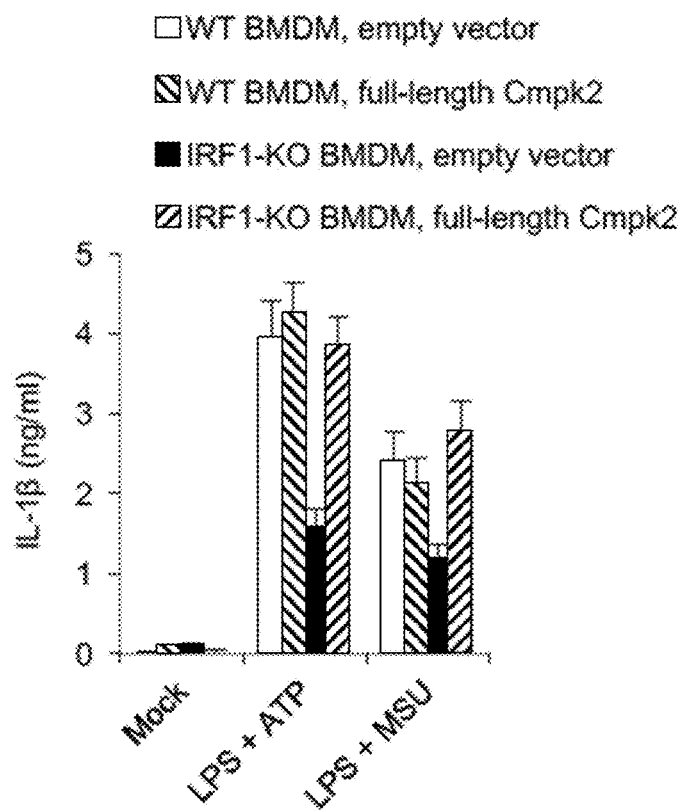
Figure 4C:
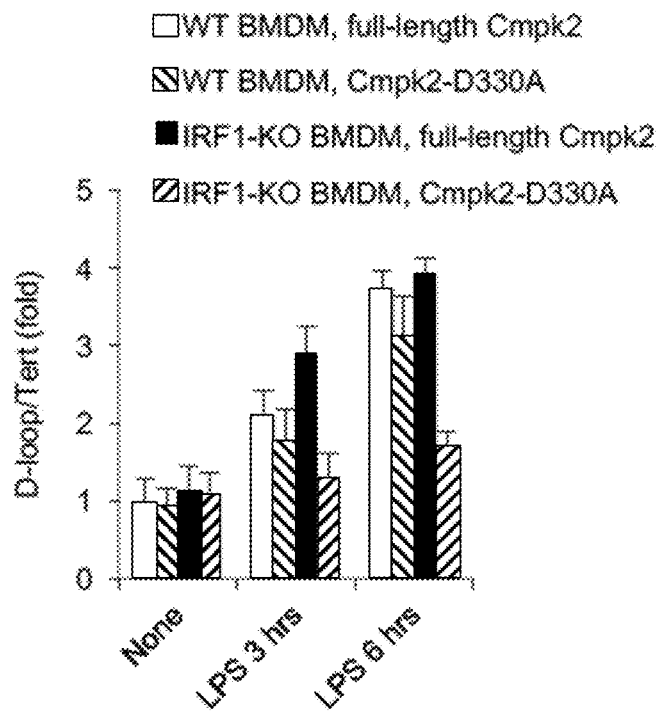
Figure 4D:
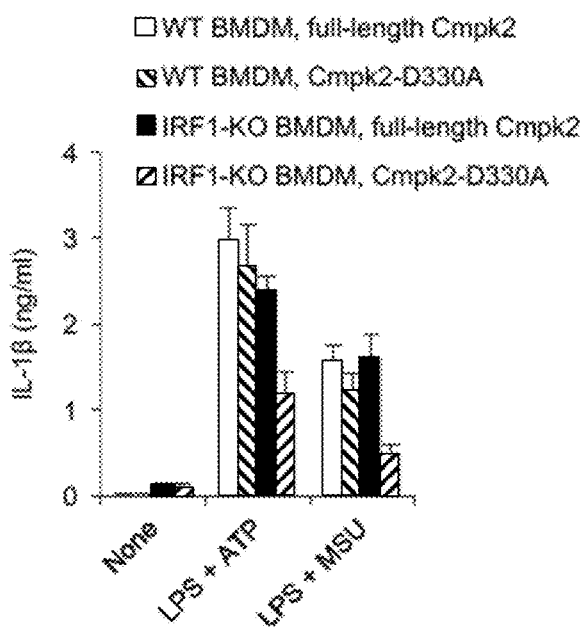
Figure 12A:
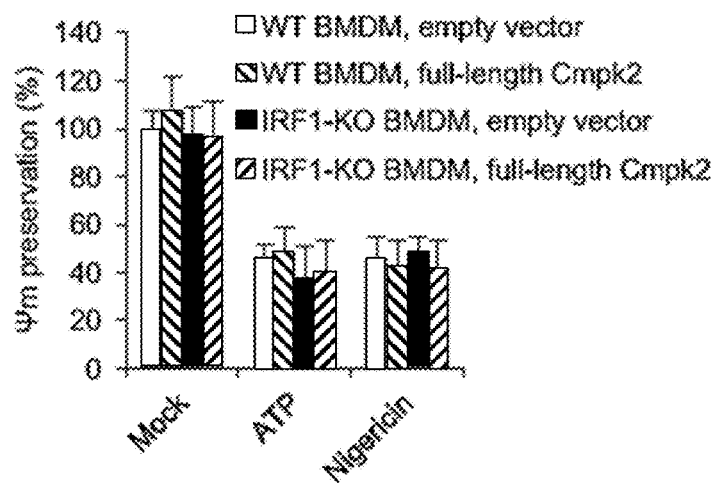
FIGS. 12A and 12B are graphical diagrams showing that expression of CMPK2 restores NLRP3 inflammasome activation in IRF1-deficient macrophages. IB analysis of CMPK2, pro-IL-1β, NLRP3, ASC, and pro-Casp1 in lysates of WT and Irf1$^{-/-}$ BMDM before and after transduction with the WT Cmpk2 lentivirus.
Figure 12B:
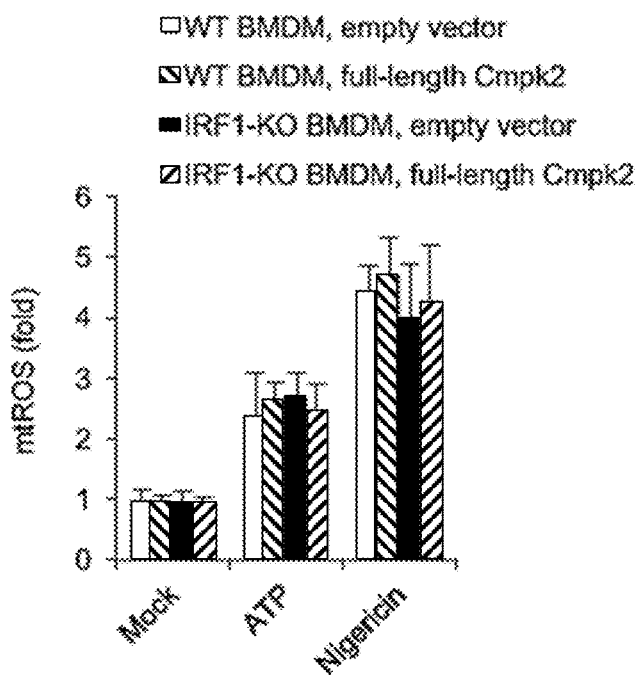

CMPK2 Catalytic Activity is Required for IRF1-Dependent NLRP3 Inflammasome Activation To confirm that CMPK2 expression promotes NLRP3 inflammasome activation by providing dCTP for mtDNA synthesis, it was decided to generate a catalytically inactive CMPK2 variant, CMPK2(D330A), by replacing the highly conserved aspartate (D) residue in its catalytic pocket (Xu et al., 2008; Chen et al., 2008) with alanine (A). Expression of WT CMPK2 in Irf1$^{-/-}$ BMDM restored LPS-stimulated mtDNA replication, but did not enhance it beyond its normal level when expressed in WT BMDM (FIG. 4A). Although CMPK2 reconstitution did not alter expression of pro-IL-1β, NLRP3, ASC, and pro-caspase-1 and had no effect on induction of mitochondrial damage by NLRP3 inflammasome activators (FIG. 12B-12C), it restored Ox-mtDNA production and NLRP3 inflammasome activation (FIG. 4A-4B). By contrast, re-expression of CMPK2(D330A) did not restore LPS-induced mtDNA synthesis, Ox-mtDNA production or NLRP3 inflammasome activation, although it did not block these responses when expressed in WT BMDM (FIG. 4C-4D). The data presented herein show strong support the notion that induction of new mtDNA replication, which depends on CMPK2 catalytic activity, is required for production of Ox-mtDNA by mitochondria that have been damaged upon macrophage exposure to "NLRP3 agonists", with Ox-mtDNA being responsible for subsequent NLRP3 inflammasome activation.

Example 5

Newly Synthesized mtDNA Associates with NLRP3 Upon Mitochondrial Damage

Figure 5:
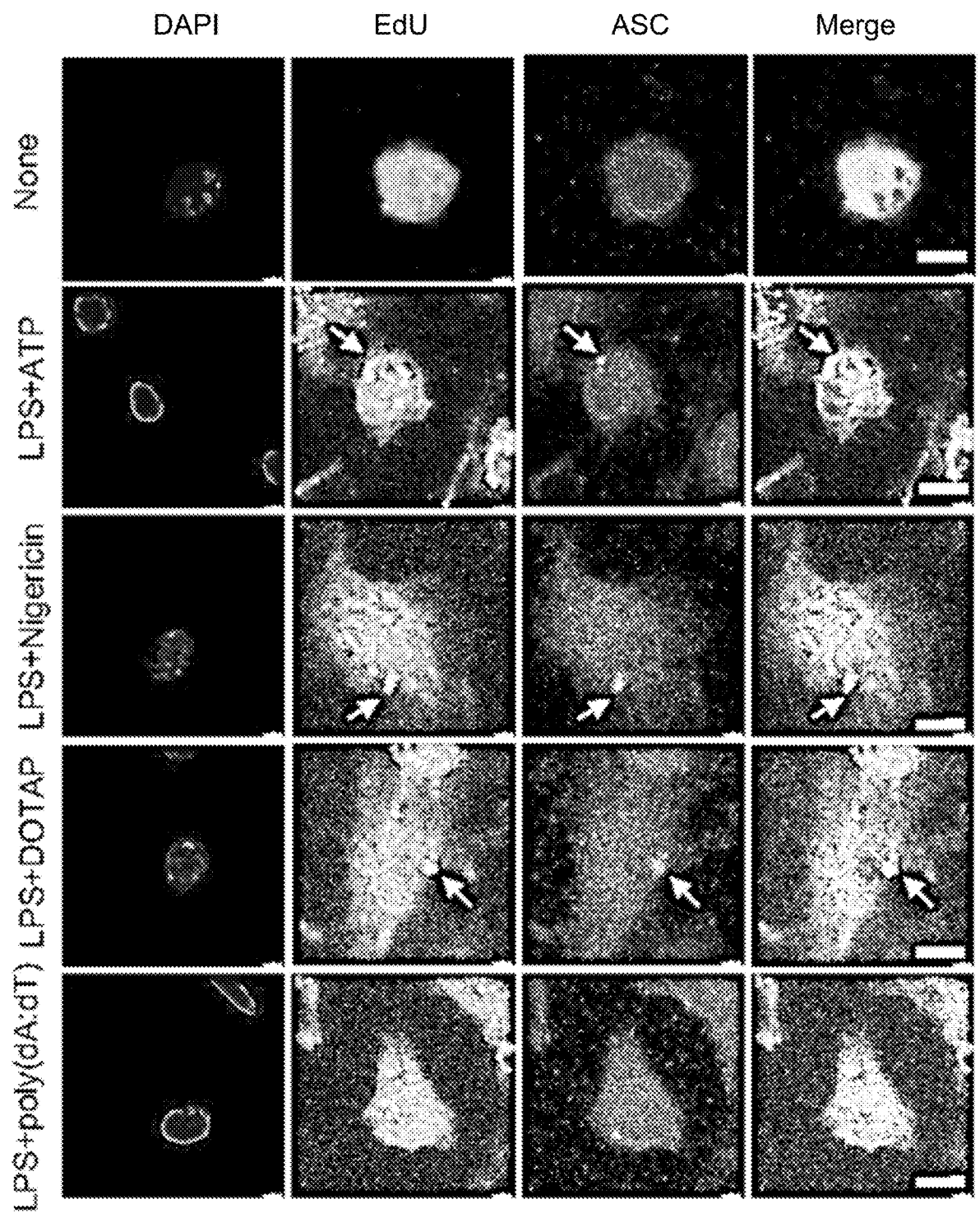
FIG. 5 is a pictorial diagram showing that newly synthesized mtDNA associated with the NLRP3 inflammasome upon mitochondrial damage. As shown, representative IF images of EdU-prelabeled BMDM were co-stained with ASC and DAPI before and after stimulation with LPS plus the indicated inflammasome activators. Scale bars, 5 μm.

To further determine the role of newly synthesized mtDNA in NLRP3 inflammasome activation, it was decided to incubate WT BMDM with BrdU (bromo-deoxyuridine) to label newly synthesized mtDNA. It was decided to stimulate the cells with LPS+ATP or LPS+nigericin and immunoprecipitated inflammasomes with antibodies to ASC. The resulting immunecomplexes were positive for both NLRP3 and BrdU labeled DNA (FIG. 5). However, when ASC was immunoprecipitated from BMDM that were stimulated with the AIM2 agonist poly(dA:dT) neither NLRP3 nor BrdU were present in the immunecomplexes. To visualize the interaction between newly synthesized mtDNA and the NLRP3 inflammasome, the cellular localization of ASC-containing inflammasome aggregates and EdU-labeled mtDNA were examined before and after NLRP3 agonist treatment. Remarkably, the NLRP3 activators ATP and nigericin induced co-localization of newly synthesized mtDNA and ASC specks, whereas the AIM2 agonist poly(dA:dT) failed to do so. The data presented herein show that the results together with the above genetic and biochemical data collectively suggest that newly synthesized mtDNA is more easily cleaved and oxidized and once released from damaged mitochondria it binds to NLRP3 and promotes inflammasome activation.

Example 6

Figure 13A:
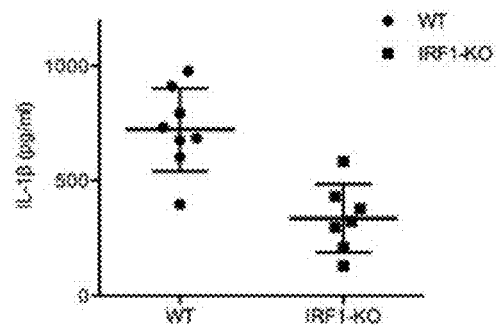
FIGS. 13A-13F are graphical diagrams showing that IRF1 controls mtDNA replication and NLRP3 inflammasome activation in vivo.
Figure 13B:
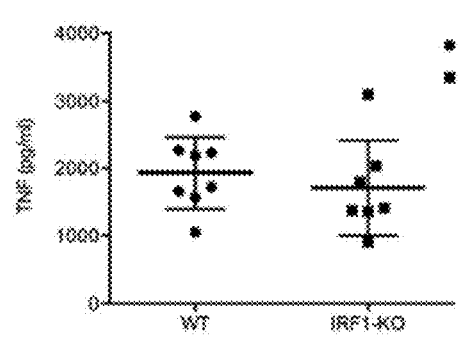
Figure 13C:
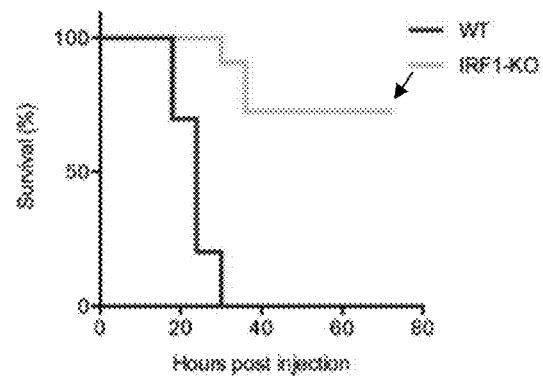
Figure 13D:
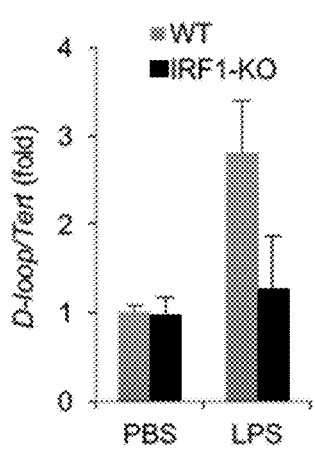
Figure 13E:
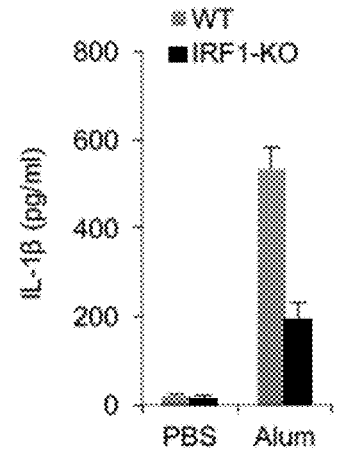
Figure 13F:
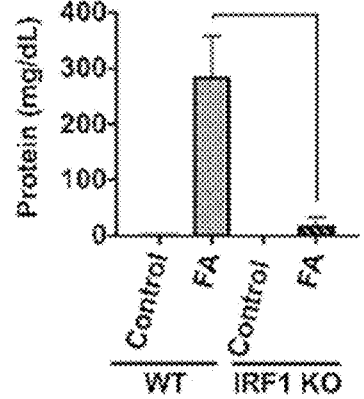

IRF1 is Required for mtDNA Replication and NLRP3 Inflammasome Activation In Vivo It was decided to examine the requirement of IRF1 signaling for NLRP3 inflammasome activation in vivo. Intraperitoneal (i.p.) injection of LPS is sufficient for induction of an IL-1β and NLRP3-dependent acute systemic inflammation that eventually leads to death (Lamkanfi and Dixit, 2012; Martinon et al., 2009). Relative to WT mice, Irf1$^{-/-}$ mice exhibited drastically reduced IL-1β secretion but little change in TNF production and were largely resistant to LPS-induced death (FIGS. 13A-13C). Importantly, Irf1$^{-/-}$ peritoneal macrophages isolated 3 hrs after LPS injection exhibited lower mtDNA copy number than macrophages from WT mice (FIG. 13D). Irf1$^{-/-}$ mice were also defective in alum-induced IL-1β production and consequently exhibited reduced neutrophil and monocyte infiltration relative to WT counterparts (FIG. 13E). Similarly, Irf1$^{-/-}$ mice were also resistant to folic acid-induced acute kidney injury (FIG. 13F), whose pathological development is NLRP3 inflammasome-dependent (Subramanian et al., 2013).

REFERENCES

Gross, et al. (2011). The inflammasome: an integrated view. Immunological reviews 243, 136-151.

Grivennikov, S. I., Greten, F. R. and Karin, M. (2010). Immunity, inflammation, and cancer. Cell 140, 883-99.

Kotas, M. E. and Medzhitov, R. (2015). Homeostasis, inflammation, and disease susceptibility. Cell 160, 816-827.

Karin, M. and Clevers, H. (2016). Reparative inflammation takes charge of tissue regeneration. Nature 529, 307-315.

Zhong, et al. (2016). Autophagy, Inflammation, and Immunity: A Troika Governing Cancer and Its Treatment. Cell 166, 288-298.

Lu, et al. (2014). Unified polymerization mechanism for the assembly of ASC-dependent inflammasomes. Cell 156, 1193-1206.

Heneka, et al. (2014). Innate immune activation in neurodegenerative disease. Nature reviews. Immunology 14, 463-477.

Lamkanfi, M. and Dixit, V. M. (2010). Inflammasomes and their roles in health and disease. Annual review of cell and developmental biology 28, 137-161.

Martinon, et al. (2009). The inflammasomes: guardians of the body. Annual review of immunology 27, 229-265.

Schroder, K. and Tschopp, J. (2010). The inflammasomes. Cell 140, 821-832.

Latz, et al. (2013). Activation and regulation of the inflammasomes. Nature reviews. Immunology 13, 397-411.

Nakahira, et al. (2011). Autophagy proteins regulate innate immune responses by inhibiting the release of mitochondrial DNA mediated by the NALP3 inflammasome. Nature immunology 12, 222-230.

Zhong, et al. (2016). NF-kappaB Restricts Inflammasome Activation via Elimination of Damaged Mitochondria. Cell 164, 896-910.

Zhou, et al. (2011). A role for mitochondria in NLRP3 inflammasome activation. Nature 469, 221-225.

Shimada, et al. (2012). Oxidized mitochondrial DNA activates the NLRP3 inflammasome during apoptosis. Immunity 36, 401-414.

Jiang, X. and Wang, X. (2004). Cytochrome C-mediated apoptosis. Annu Rev Biochem 73, 87-106.

Hamanaka, et al. (2013). Mitochondrial reactive oxygen species promote epidermal differentiation and hair follicle development. Sci Signal 6, ra8.

Hudson, G. and Chinnery, P. F. (2006). Mitochondrial DNA polymerase-gamma and human disease. Hum Mol Genet 15 Spec No 2, R244-252.

Kawai, T. and Akira, S. (2010). The role of pattern-recognition receptors in innate immunity: update on Toll-like receptors. Nature immunology 11, 373-384.

Ullah, et al. (2016). TRIF-dependent TLR signaling, its functions in host defense and inflammation, and its potential as a therapeutic target. J Leukoc Biol 100, 27-45.

Jehl, et al. (2012). IFNgamma inhibits the cytosolic replication of *Shigella flexneri* via the cytoplasmic RNA sensor RIG-I. PLoS Pathog 8, e1002809.

Xu, et al. (2008). Human UMP-CMP kinase 2, a novel nucleoside monophosphate kinase localized in mitochondria. The Journal of biological chemistry 283, 1563-1571.

Milon, et al. (2000). The human nm23-H4 gene product is a mitochondrial nucleoside diphosphate kinase. The Journal of biological chemistry 275, 14264-14272.

Chen, et al. (2008). Identification of a putative human mitochondrial thymidine monophosphate kinase associated with monocytic/macrophage terminal differentiation. Genes to cells: devoted to molecular & cellular mechanisms 13, 679-689.

Subramanian, et al. (2013). The adaptor MAVS promotes NLRP3 mitochondrial localization and inflammasome activation. Cell 153, 348-361.

Elliott, E. I. and Sutterwala, F. S. (2015). Initiation and perpetuation of NLRP3 inflammasome activation and assembly. Immunological reviews 265, 35-52.

West, et al. (2011). TLR signalling augments macrophage bactericidal activity through mitochondrial ROS. Nature 472, 476-480.

Although the invention has been described with reference to the above examples, it will be understood that modifications and variations are encompassed within the spirit and scope of the invention. Accordingly, the invention is limited only by the following claims.

---

What is claimed is:

1. A method of treating nod-like receptor pyrin domain containing 3 (NLRP3) inflammasome-associated inflammatory and/or degenerative diseases in a subject in need thereof comprising administering to the subject an effective amount of an inhibitor of cytidine monophosphate kinase 2 (CMPK2) activity or expression.

2. The method of claim 1, wherein the inhibitor of CMPK2 activity or expression is a small molecule, nucleotide analog, peptide, antisense oligonucleotide, antibody or antibody fragment.

3. The method of claim 2, wherein the inhibitor of CMPK2 activity or expression is an inhibitory nucleic acid that inhibits the expression of CMPK2 or inhibits CMPK2 synthesis.

4. The method of claim 3, wherein the inhibitory nucleic acid is selected from the group consisting of siRNA, shRNA, gRNA, oligonucleotides, antisense RNA or ribozymes that inhibit CMPK2 synthesis.

5. The method of claim 4, wherein the inhibitory nucleic acid is administered via a viral vector, a liposome or a nanoparticle.

6. The method of claim 1, wherein the subject is a mammal.

7. The method of claim 6, wherein the mammal is a human.

8. The method of claim 7, wherein the subject suffers from an NLRP3 inflammasome-associated inflammatory and/or degenerative disease that is selected from the group consisting of cancer, lupus, gout, rheumatoid arthritis, osteoarthritis, ankylosing spondylitis, uveitis, Alzheimer's disease, Parkinson's disease, cryopyrin-associated periodic syndromes, nonalcoholic steatohepatitis (NASH), type 2 diabetes, atherosclerosis, and macular degeneration.

9. A method of inhibiting NLRP3 inflammasome activation in a subject comprising administering to the subject an effective amount of an inhibitor of CMPK2 activity or expression.

10. The method of claim 9, wherein the inhibitor of CMPK2 activity or expression is a small molecule, nucleotide analog, peptide, antisense oligonucleotide, antibody or antibody fragment.

11. The method of claim 9, wherein the inhibitor of CMPK2 activity or expression is an inhibitory nucleic acid that inhibits the expression of CMPK2 or inhibits CMPK2 synthesis.

12. The method of claim 11, wherein the inhibitory nucleic acid is selected from the group consisting of siRNA, shRNA, gRNA, oligonucleotides, antisense RNA or ribozymes that inhibit CMPK2 synthesis.

13. The method of claim 11, wherein the inhibitory nucleic acid is administered via a viral vector.

14. The method of claim 2, wherein the inhibitor of CMPK2 activity or expression is a small molecule.

15. The method of claim 2, wherein the inhibitor of CMPK2 activity or expression is a nucleotide analog.

16. The method of claim 2, wherein the inhibitor of CMPK2 activity or expression is a peptide.

17. The method of claim 2, wherein the inhibitor of CMPK2 activity or expression is an antisense oligonucleotide.

18. The method of claim 2, wherein the inhibitor of CMPK2 activity or expression is an antibody or antibody fragment.

19. The method of claim 10, wherein the inhibitor of CMPK2 activity or expression is a small molecule.

20. The method of claim 10, wherein the inhibitor of CMPK2 activity or expression is a nucleotide analog.

21. The method of claim 10, wherein the inhibitor of CMPK2 activity or expression is a peptide.

22. The method of claim 10, wherein the inhibitor of CMPK2 activity or expression is an antisense oligonucleotide.

23. The method of claim 10, wherein the inhibitor of CMPK2 activity or expression is an antibody or antibody fragment.

* * * * *

SEQUENCE LISTING

<160> NUMBER OF SEQ ID NOS: 5

<210> SEQ ID NO 1
<211> LENGTH: 449
<212> TYPE: PRT
<213> ORGANISM: Homo sapiens

<400> SEQUENCE: 1

```
Met Ala Phe Ala Arg Arg Leu Leu Arg Gly Pro Leu Ser Gly Pro Leu
 1               5                   10                  15

Leu Gly Arg Arg Gly Val Cys Ala Gly Ala Met Ala Pro Pro Arg Arg
             20                  25                  30

Phe Val Leu Glu Leu Pro Asp Cys Thr Leu Ala His Phe Ala Leu Gly
         35                  40                  45
```

-continued

```
Ala Asp Ala Pro Gly Asp Ala Asp Ala Pro Asp Pro Arg Leu Ala Ala
         50                  55                  60
Leu Leu Gly Pro Pro Glu Arg Ser Tyr Ser Leu Cys Val Pro Val Thr
 65                  70                  75                  80
Pro Asp Ala Gly Cys Gly Ala Arg Val Arg Ala Ala Arg Leu His Gln
                 85                  90                  95
Arg Leu Leu His Gln Leu Arg Arg Gly Pro Phe Gln Arg Cys Gln Leu
                100                 105                 110
Leu Arg Leu Leu Cys Tyr Cys Pro Gly Gly Gln Ala Gly Gly Ala Gln
            115                 120                 125
Gln Gly Phe Leu Leu Arg Asp Pro Leu Asp Asp Pro Asp Thr Arg Gln
        130                 135                 140
Ala Leu Leu Glu Leu Leu Gly Ala Cys Gln Glu Ala Pro Arg Pro His
145                 150                 155                 160
Leu Gly Glu Phe Glu Ala Asp Pro Arg Gly Gln Leu Trp Gln Arg Leu
                165                 170                 175
Trp Glu Val Gln Asp Gly Arg Arg Leu Gln Val Gly Cys Ala Gln Val
            180                 185                 190
Val Pro Val Pro Glu Pro Leu His Pro Val Pro Asp Leu Pro
        195                 200                 205
Ser Ser Val Val Phe Pro Asp Arg Glu Ala Ala Arg Ala Val Leu Glu
210                 215                 220
Glu Cys Thr Ser Phe Ile Pro Glu Ala Arg Ala Val Leu Asp Leu Val
225                 230                 235                 240
Asp Gln Cys Pro Lys Gln Ile Gln Lys Gly Lys Phe Gln Val Val Ala
                245                 250                 255
Ile Glu Gly Leu Asp Ala Thr Gly Lys Thr Thr Val Thr Gln Ser Val
            260                 265                 270
Ala Asp Ser Leu Lys Ala Val Leu Leu Lys Ser Pro Pro Ser Cys Ile
        275                 280                 285
Gly Gln Trp Arg Lys Ile Phe Asp Asp Glu Pro Thr Ile Ile Arg Arg
    290                 295                 300
Ala Phe Tyr Ser Leu Gly Asn Tyr Ile Val Ala Ser Glu Ile Ala Lys
305                 310                 315                 320
Glu Ser Ala Lys Ser Pro Val Ile Val Asp Arg Tyr Trp His Ser Thr
                325                 330                 335
Ala Thr Tyr Ala Ile Ala Thr Glu Val Ser Gly Gly Leu Gln His Leu
            340                 345                 350
Pro Pro Ala His His Pro Val Tyr Gln Trp Pro Glu Asp Leu Leu Lys
        355                 360                 365
Pro Asp Leu Ile Leu Leu Leu Thr Val Ser Pro Glu Glu Arg Leu Gln
    370                 375                 380
Arg Leu Gln Gly Arg Gly Met Glu Lys Thr Arg Glu Glu Ala Glu Leu
385                 390                 395                 400
Glu Ala Asn Ser Val Phe Arg Gln Lys Val Glu Met Ser Tyr Gln Arg
                405                 410                 415
Met Glu Asn Pro Gly Cys His Val Val Asp Ala Ser Pro Ser Arg Glu
            420                 425                 430
Lys Val Leu Gln Thr Val Leu Ser Leu Ile Gln Asn Ser Phe Ser Glu
        435                 440                 445
Pro
```

```
<210> SEQ ID NO 2
<211> LENGTH: 325
<212> TYPE: PRT
<213> ORGANISM: Homo sapiens

<400> SEQUENCE: 2

Met Pro Ile Thr Arg Met Arg Met Arg Pro Trp Leu Glu Met Gln Ile
1               5                   10                  15

Asn Ser Asn Gln Ile Pro Gly Leu Ile Trp Ile Asn Lys Glu Glu Met
            20                  25                  30

Ile Phe Gln Ile Pro Trp Lys His Ala Ala Lys His Gly Trp Asp Ile
        35                  40                  45

Asn Lys Asp Ala Cys Leu Phe Arg Ser Trp Ala Ile His Thr Gly Arg
    50                  55                  60

Tyr Lys Ala Gly Glu Lys Glu Pro Asp Pro Lys Thr Trp Lys Ala Asn
65                  70                  75                  80

Phe Arg Cys Ala Met Asn Ser Leu Pro Asp Ile Glu Glu Val Lys Asp
                85                  90                  95

Gln Ser Arg Asn Lys Gly Ser Ser Ala Val Arg Val Tyr Arg Met Leu
            100                 105                 110

Pro Pro Leu Thr Lys Asn Gln Arg Lys Glu Arg Lys Ser Lys Ser Ser
        115                 120                 125

Arg Asp Ala Lys Ser Lys Ala Lys Arg Lys Ser Cys Gly Asp Ser Ser
130                 135                 140

Pro Asp Thr Phe Ser Asp Gly Leu Ser Ser Ser Thr Leu Pro Asp Asp
145                 150                 155                 160

His Ser Ser Tyr Thr Val Pro Gly Tyr Met Gln Asp Leu Glu Val Glu
                165                 170                 175

Gln Ala Leu Thr Pro Ala Leu Ser Pro Cys Ala Val Ser Ser Thr Leu
            180                 185                 190

Pro Asp Trp His Ile Pro Val Glu Val Val Pro Asp Ser Thr Ser Asp
        195                 200                 205

Leu Tyr Asn Phe Gln Val Ser Pro Met Pro Ser Thr Ser Glu Ala Thr
210                 215                 220

Thr Asp Glu Asp Glu Gly Lys Leu Pro Glu Asp Ile Met Lys Leu
225                 230                 235                 240

Leu Glu Gln Ser Glu Trp Gln Pro Thr Asn Val Asp Gly Lys Gly Tyr
                245                 250                 255

Leu Leu Asn Glu Pro Gly Val Gln Pro Thr Ser Val Tyr Gly Asp Phe
            260                 265                 270

Ser Cys Lys Glu Glu Pro Glu Ile Asp Ser Pro Gly Gly Asp Ile Gly
        275                 280                 285

Leu Ser Leu Gln Arg Val Phe Thr Asp Leu Lys Asn Met Asp Ala Thr
290                 295                 300

Trp Leu Asp Ser Leu Leu Thr Pro Val Arg Leu Pro Ser Ile Gln Ala
305                 310                 315                 320

Ile Pro Cys Ala Pro
                325

<210> SEQ ID NO 3
<211> LENGTH: 10
<212> TYPE: DNA
<213> ORGANISM: Artificial Sequence
<220> FEATURE:
<223> OTHER INFORMATION: synthetic construct
```

```
<400> SEQUENCE: 3
ttttgttttt                                                      10

<210> SEQ ID NO 4
<211> LENGTH: 11
<212> TYPE: DNA
<213> ORGANISM: Artificial Sequence
<220> FEATURE:
<223> OTHER INFORMATION: synthetic construct

<400> SEQUENCE: 4
aggaaagggg a                                                    11

<210> SEQ ID NO 5
<211> LENGTH: 10
<212> TYPE: DNA
<213> ORGANISM: Artificial Sequence
<220> FEATURE:
<223> OTHER INFORMATION: synthetic construct

<400> SEQUENCE: 5
tttcatttct                                                      10
```